(12) United States Patent
Hey et al.

(10) Patent No.: US 6,906,081 B2
(45) Date of Patent: Jun. 14, 2005

(54) USE OF DUAL $H_3/M_2$ ANTAGONISTS IN THE TREATMENT OF COGNITION DEFICIT DISORDERS

(75) Inventors: John A. Hey, Randolph, NJ (US); Robert G. Aslanian, Rockaway, NJ (US)

(73) Assignee: Schering Corporation, Kenilworth, NJ (US)

( * ) Notice: Subject to any disclaimer, the term of this patent is extended or adjusted under 35 U.S.C. 154(b) by 94 days.

(21) Appl. No.: 10/072,340

(22) Filed: Feb. 6, 2002

(65) Prior Publication Data

US 2002/0151565 A1 Oct. 17, 2002

Related U.S. Application Data

(60) Provisional application No. 60/267,352, filed on Feb. 8, 2001.

(51) Int. Cl.[7] ........................ A61K 31/44; A61K 31/445
(52) U.S. Cl. ........................................ 514/297; 514/316
(58) Field of Search .................................. 514/297, 316

(56) References Cited

U.S. PATENT DOCUMENTS

| | | | |
|---|---|---|---|
| 2,624,734 A | | 1/1953 | Goldberg et al. |
| 5,352,707 A | | 10/1994 | Pompni et al. |
| 5,446,057 A | | 8/1995 | Augelli-Szafran et al. |
| 5,463,074 A | | 10/1995 | Shih et al. |
| 5,578,616 A | | 11/1996 | Aslanian et al. |
| 5,633,250 A | | 5/1997 | Shih et al. |
| 5,807,872 A | | 9/1998 | Shih et al. |
| 5,883,096 A | * | 3/1999 | Lowe et al. |
| 5,889,006 A | | 3/1999 | Lowe et al. |
| 5,935,958 A | | 8/1999 | Kozlowski et al. |
| 5,952,349 A | | 9/1999 | Asberom et al. |
| 5,977,138 A | | 11/1999 | Wang et al. |
| 5,990,147 A | | 11/1999 | Aslanian et al. |
| 6,034,251 A | | 3/2000 | Aslanian et al. |
| 6,037,352 A | | 3/2000 | Lowe et al. |
| 6,043,255 A | | 3/2000 | Lowe et al. |
| 6,066,636 A | | 5/2000 | Kozlowski et al. |
| 6,100,279 A | | 8/2000 | Vaccaro et al. |
| 6,294,554 B1 | | 9/2001 | Clader et al. |

FOREIGN PATENT DOCUMENTS

| EP | 0 420 396 A2 | 4/1991 |
|---|---|---|
| WO | WO 93/01812 | 2/1993 |

OTHER PUBLICATIONS

Drug Facts and Comparisons, 1999 edition, p. 1731.*
Craig D. Boyle et al., Bioorganic & Medicinal Chemistry Letters, 10 pp. 2727–2730 (2000).
Stephen L. Yates et al., The Journal of Pharmacology & Experimental Therapeutics, 289 (2), pp. 1151–1159 (1999).
X. Ligneau et al., The Journal of Pharmacology & Experimental Therapeutics 287, (2) pp. 658–666 (1998).
Rob Leurs et al., Elsevier Science Ltd., 19, pp. 177–184 (1998).
Maria Grazia Giovannini et al., Behavioural Brain Research 104, pp. 147–155 (1999).
Susan R. McGurk, Ph.D., J. Clin Psychiatry 60 (suppl 12), pp 24–29 (1999).
Nita Nacasch et al., Clinical Neuropharmacology, 21, (2) pp. 132–134 (1998).
Folia Pharmacol. Jpn., 114, pp. 89–106 (1999)—XP 008021117.
William Howson et al., Bioorg. & Med. Chem. Letters, vol. 2, No. 1, (1992), pp. 77–78.
Van der Goot et al., Eur J. Med Chem (1992) vol. 27, pp. 511–517.
Clapham et al., J. Psychopharmacol. British Assn. For Psychopharmacology, Jul. 25–28, 1993, Asbstr. Book, A17.
Clapham et al., Brit. J. Pharm. Suppl., 1993, 110, Abstr. 65P.
Yokoyama et al, Eur. J. Pharmacol., vol. 234 (1993), pp. 129–133.
Schlicker et al., Br. J. Pharmacol. (1994), 112, pp. 1043–1048.
Leurs et al., Progr. Drug Res. (1992) vol. 39, pp. 127–165.
Lipp et al. The Histamine Receptor, eds.: Schwartz and Haas, Wiley–Liss, New York, (1992), pp. 57–72.
West et al., Molecular Pharmacology, vol. 38, (1990), pp. 610–613.
Korte et al., Biochemical and Biophysical Research Communications, vol. 168, (1990), pp. 979–986.

* cited by examiner

Primary Examiner—San-ming Hui
(74) Attorney, Agent, or Firm—Anita W. Magatti

(57) ABSTRACT

This invention relates to a method of treating cognition deficit disorders comprising administering to a mammal in need of such treatment an effective amount of a dual histamine $H_3$ receptor antagonist/$m_2$ muscarinic antagonist, or a combination of a histamine $H_3$ receptor antagonist and a $m_2$ muscarinic antagonist.

4 Claims, No Drawings

USE OF DUAL H₃/M₂ ANTAGONISTS IN THE TREATMENT OF COGNITION DEFICIT DISORDERS

CROSS REFERENCE TO RELATED APPLICATION

This application claims the benefit of U.S. Provisional Application 60/267,352, filed Feb. 8, 2001.

BACKGROUND

This invention relates to the treatment of cognition deficit disorders by administering a dual histamine $H_3$ receptor antagonist/$m_2$ muscarinic antagonist, or a combination of an histamine $H_3$ receptor antagonist and a $m_2$ muscarinic antagonist. In particular, the invention relates to the treatment of cognition deficit diseases such as Alzheimer's Disease (AD) or other CNS learning disorders such as attention deficit disorder and autism.

European Patent Application No. 0 420 396 A2 and Howson et al., *Bioorg. & Med. Chem. Letters,* Vol. 2 No. 1 (1992), pp. 77–78, describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine $H_3$ receptor, and these isothiourea analogs of histamine overlap in part with those of the two references cited above. Clapham et al, *J. Psychopharmacol.* (British Assn. for Psychopharmacology, Jul. 25–28 1993, Abstr. Book), A17] describes the ability of histamine $H_3$ receptor antagonists to improve cognition and to increase release of acetylcholine in vivo in the rat. Clapham et al., *Brit. J. Pharm. Suppl.,* 1993, 110, Abstract 65P, presents results showing that thioperamide can improve short-term memory and reversal learning in the rat and implicate the involvement of $H_3$ receptors in the modulation of cognitive function. Yokoyama et al, *Eur. J. Pharmacol.,* vol. 234 (1993), pp. 129–133, reports how thioperamide decreased the duration of each phase of convulsion and raised the electroconvulsive threshold, and go on to suggest that these and other findings support the hypothesis that the central histaminergic system is involved in the inhibition of seizures. WO 9301812-A1 describes the use of S-[3-(4(5)-imidazolyl)propyl]-isothiourea as a histamine $H_3$ antagonist, especially for treating cognitive disorders, e.g. Alzheimer's disease and age-related memory impairment. Schlicker et al. describe a number of imidazolylalkyl compounds wherein the imidazolylalkyl group is bonded to a guanidine group, an ester group or an amide group (including thioamide and urea), and compare these to thioperamide. Leurs et al., *Progr. Drug Res.* (1992) vol. 39, pp. 127–165, and Lipp et al. *The Histamine Receptor,* eds.: Schwartz and Haas, Wiley-Liss, New York (1992), pp. 57–72, review a variety of synthetic $H_3$ receptor antagonists, and Lipp et al. (ibid. ) have defined the necessary structural requirements for an $H_3$ receptor antagonist.

Several muscarinic receptor subtypes have been identified, i.e., $m_1$, $m_2$, $m_3$, $m_4$ and $m_5$, and the potential therapeutic effects of the various subtypes have been the subject of many publications. See, for example, U.S. Pat. No. 5,446,057, wherein the $m_1$ receptor was identified as mediating gastric secretion; $m_2$ and $m_3$ receptors were identified as mediating nasal mucosal secretions; and $m_2$ was identified as mediating cardiovascular conditions and CNS conditions associated with release of acetylcholine, e.g., Alzheimer's disease and other dementias. Muscarinic receptors in general were reported to be mediators of cholinergic neurotransmission.

SUMMARY OF THE INVENTION

This invention relates to a method of treating cognition deficit disorders comprising administering to a mammal in need of such treatment an effective amount of a dual histamine $H_3$ receptor antagonist/$m_2$ muscarinic antagonist, or a combination of an histamine $H_3$ receptor antagonist and a $m_2$ muscarinic antagonist. In particular, the method relates to the treatment of Alzheimer's Disease, attention deficit disorder or autism comprising administering an effective amount of a dual $H_3/m_2$ antagonist, or a combination of an $H_3$ antagonist and a $m_2$ antagonist.

The dual $H_3/m_2$ antagonist compounds of the invention are preferably administered as a pharmaceutical composition comprising the dual antagonist and a pharmaceutically acceptable carrier. When separate $H_3$ and $m_2$ antagonists are used in combination, an effective amount of the combination of a $H_3$ antagonist and a $m_2$ antagonist can be combined with a pharmaceutically acceptable carrier in a single pharmaceutical composition. Alternatively, a pharmaceutical composition comprising a $H_3$ antagonist and a separate pharmaceutical composition comprising a $m_2$ antagonist can be administered, simultaneously or sequentially, wherein the individual antagonists are administered in amounts chosen so that the combination is effective to treat cognition deficit disorders. Kits comprising separate $H_3$ and $m_2$ pharmaceutical compositions in a single package are also contemplated.

In still another aspect, the invention relates to a method for treating a cognitive disease or neurodegenerative disease comprising administering to a mammal in need of such treatment an effective amount of a dual histamine $H_3$ receptor antagonist/$m_2$ muscarinic antagonist, or a combination of an histamine $H_3$ receptor antagonist and a $m_2$ muscarinic antagonist, in further combination with an acetylcholinesterase inhibitor. Pharmaceutical compositions comprising a dual histamine $H_3$ receptor antagonist/$m_2$ muscarinic antagonist and an acetylcholinesterase inhibitor in a pharmaceutically acceptable carrier, or separate $H_3$ and $m_2$ antagonists and an acetylcholinesterase inhibitor in a pharmaceutically acceptable carrier are contemplated. Kits comprising separate dual $H_3/m_2$ antagonist and acetylcholinesterase inhibitor pharmaceutical compositions, and separate $H_3$, $m_2$ and acetylcholinesterase inhibitor pharmaceutical compositions in a single package are also contemplated.

DETAILED DESCRIPTION

Dual $H_3/m_2$ antagonists of the present invention are exemplified by the compounds shown in the following table:

| Compound Number | Structure |
|---|---|
| 1 | 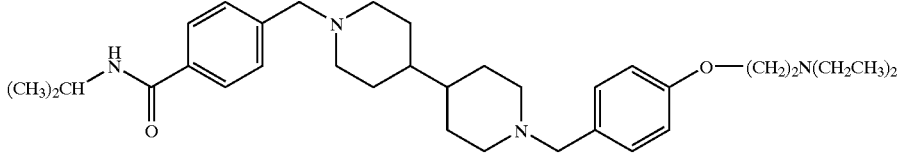 |
| 2 | 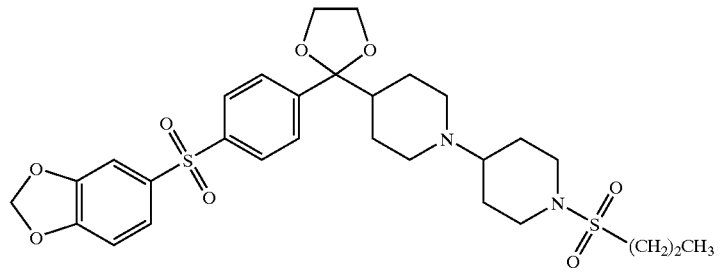 |
| 3 | 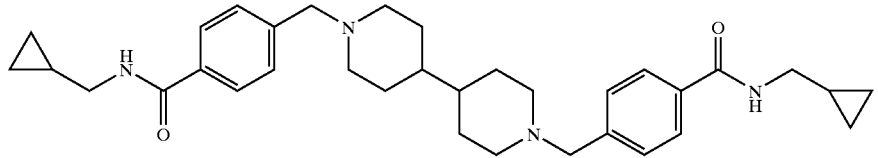 |
| 4 | 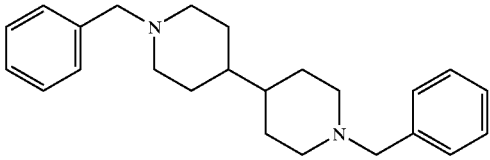 |
| 5 | 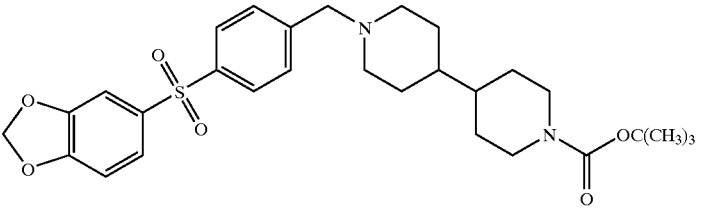 |
| 6 | 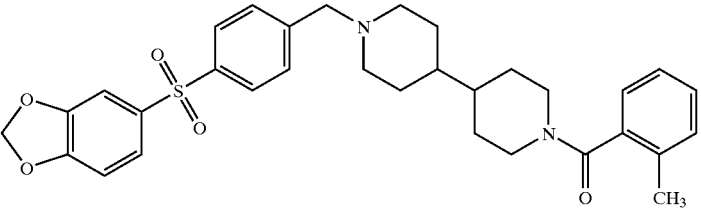 |
| 7 | 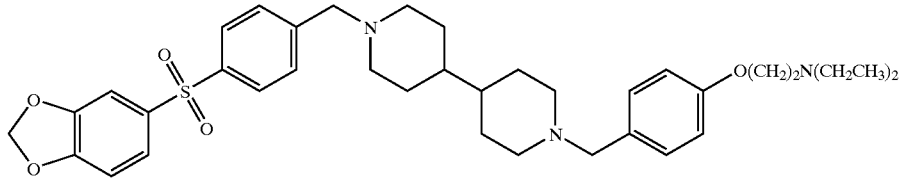 |

-continued

| Compound Number | Structure |
|---|---|
| 8 | 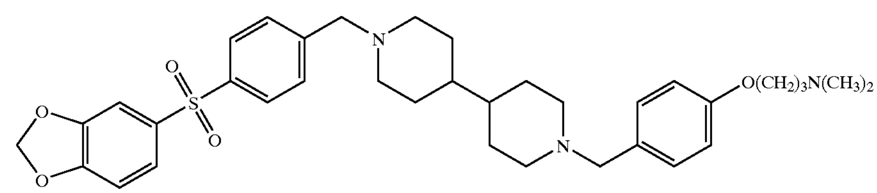 |
| 9 | 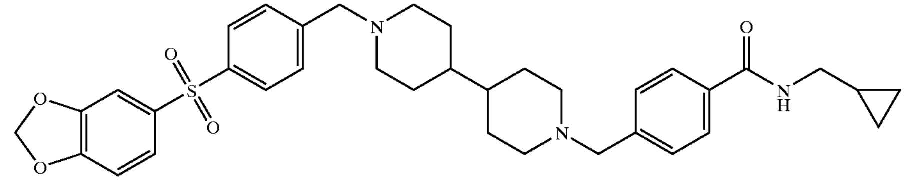 |
| 10 | 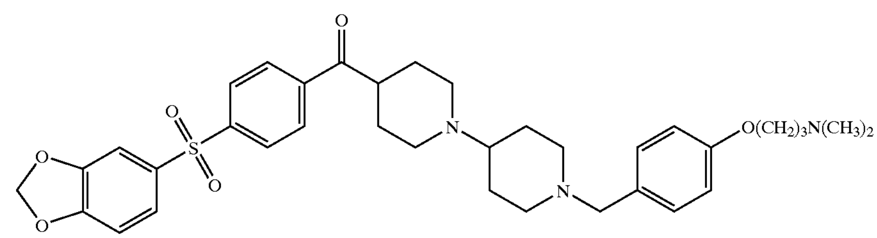 |
| 11 | 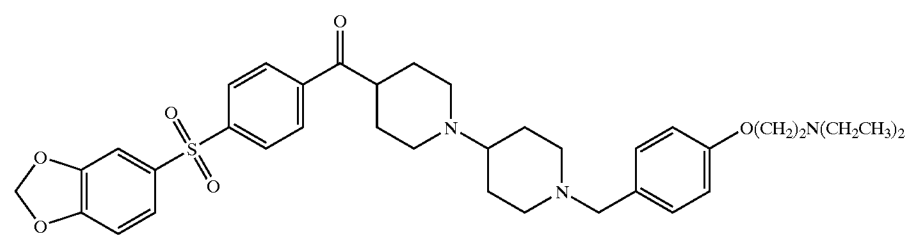 |
| 12 | 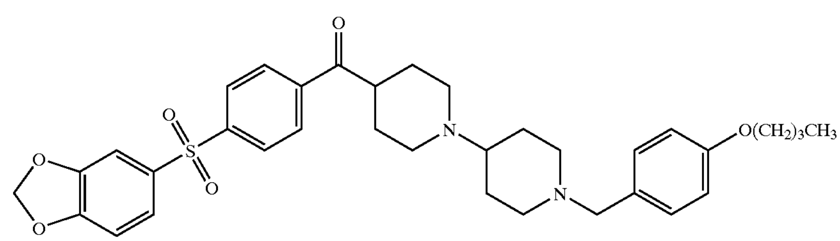 |
| 13 | 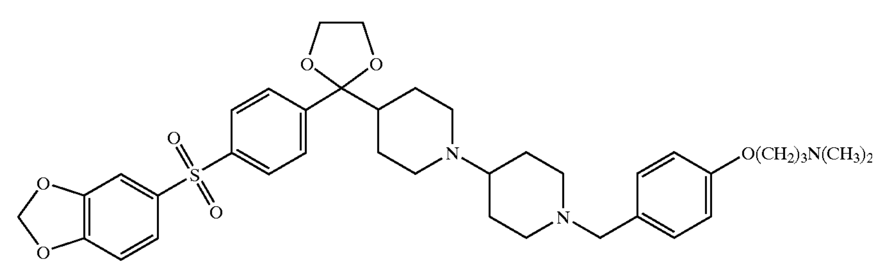 |

| Compound Number | Structure |
|---|---|
| 14 | 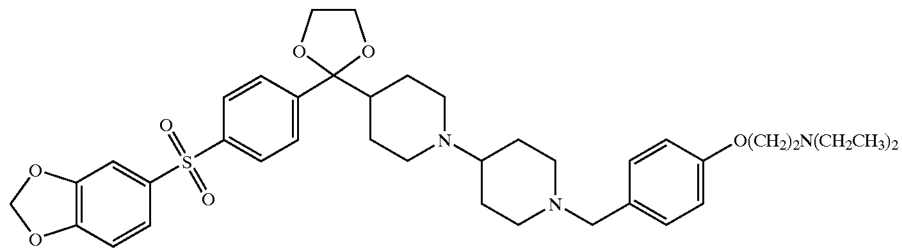 |
| 15 | 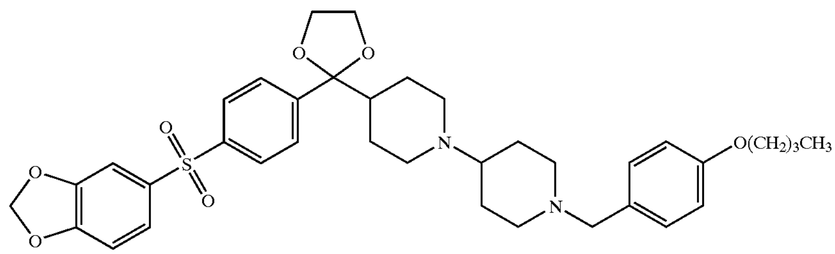 |

Other compounds having dual $H_3/m_2$ antagonist activity can be identified by evaluating the compounds for activity at $H_3$ receptors and activity at $m_2$ receptors using the test methods described below.

The currently known histamine $H_3$ receptor antagonists cannot be easily classified chemically, but include, without limitation: thioperamide, impromidine, burimamide, clobenpropit, impentamine, mifetidine, clozapine, S-sopromidine, R-sopromidine, ciproxifam, SKF-91486, GR-175737, GT-2016, GT-2331 and UCL-1199.

Certain $H_3$ antagonists are disclosed in several U.S. patents. U.S. Pat. No. 5,463,074 discloses the following compounds:

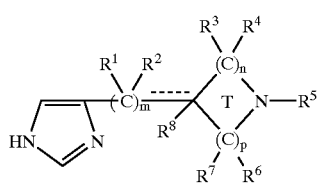

I or a pharmaceutically acceptable salt or solvate thereof, wherein:

(A) m is an integer selected from the group consisting of: 0, 1, and 2;

(B) n and p are integers and are each independently selected from the group consisting of: 0, 1, 2, and 3 such that the sum of n and p is 2 or 3;

(C) each $R^1$, $R^2$, $R^3$, $R^4$, $R^6$, $R^7$, and $R^8$ is independently selected from the group consisting of:

(1) H;

(2) $C_1$ to $C_6$ alkyl;

(3) $C_3$ to $C_6$ cycloalkyl; and (4) —$(CH_2)_q$—$R^9$ wherein q is an integer of: 1 to 7, and $R^9$ is selected from the group consisting of: phenyl, substituted phenyl, —$OR^{10}$, —$C(O)OR^{10}$, —$C(O)R^{10}$, —$OC(O)R^{10}$, —$C(O)NR^{10}R^{11}$, CN and —$SR^{10}$ wherein $R^{10}$ and $R^{11}$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains from 1 to 3 substituents;

(D) $R^5$ is selected from the group consisting of:

(1) H;

(2) $C_1$ to $C_{20}$ alkyl;

(3) $C_3$ to $C_6$ cycloalkyl;

(4) —$C(O)OR^{10'}$; wherein $R^{10'}$ is the same as $R^{10}$ defined below except that $R^{10'}$ is not H;

(5) —$C(O)R^{10}$;

(6) —$C(O)NR^{10}R^{11}$;

(7) allyl;

(8) propargyl; and (9) —$(CH_2)_q$—$R^9$, wherein q and $R^9$ are as defined above with the proviso that when q is 1 then $R^9$ is not —OH or —SH;

(E) $R^{10}$ and $R^{11}$ are each independently selected from the group consisting of: H, $C_1$ to $C_6$ alkyl, and $C_3$ to $C_6$ cycloalkyl; and, for the substituent —$C(O)NR^{10}R^{11}$, $R^{10}$ and $R^{11}$, together with the nitrogen to which they are bound, can form a ring having 5, 6, or 7 atoms;

(F) the dotted line (------) represents a double bond that is optionally present when m is 1, and T is a 5-membered ring, and n is not 0, and p is not 0, and when said double bond is present then $R^2$ and $R^8$ are absent;

(G) when m is 2, each $R^1$ is the same or different substituent for each m, and each $R^2$ is the same or different substituent for each m;

(H) when n is 2 or 3, each $R^3$ is the same or different substituent for each n, and each $R^4$ is the same or different substituent for each n; and (I) when p is 2 or 3, each $R^6$ is the same or different substituent for each p, and each $R^7$ is the same or different substituent for each p.

U.S. Pat. No. 5,807,872 discloses the following compounds:

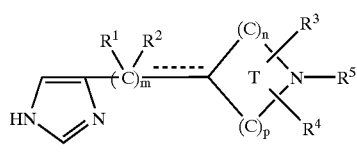

II or a pharmaceutically acceptable salt or solvate thereof, wherein:

(A) m is 1 or 2;

(B) n and p are independently selected from 0, 1, 2, 3, and 4 such that the sum of n and p is 4 and T is a 6-membered ring;

(C) $R^3$ and $R^4$ are each independently bound to the same or different carbon atom of ring T such that there is only one $R^3$ group and one $R^4$ group in ring T, and each $R^1$, $R^2$, $R^3$, and $R^4$ is independently selected from the group consisting of:

(1) H;

(2) $C_1$ to $C_6$ alkyl; and (3) —$(CH_2)_q$—$R^6$ wherein q is an integer of: 1 to 7, and $R^6$ is selected from the group consisting of: phenyl, substituted phenyl, —$OR^7$, —$C(O)OR^7$, —$C(O)R^7$, —$OC(O)R^7$, —$C(O)NR^7R^8$, CN and —$SR^7$ wherein $R^7$ and $R^8$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains 1 to 3 substituents;

(D) $R^5$ is selected from the group consisting of:

(1) H;

(2) $C_1$ to $C_{20}$ alkyl;

(3) $C_3$ to $C_6$ cycloalkyl;

(4) —$C(O)OR^{7'}$; wherein $R^{7'}$ is the same as $R^7$ defined below except that $R^{7'}$ is not H;

(5) —$C(O)R^7$;

(6) —$C(O)NR^7R^8$;

(7) allyl;

(8) propargyl; and (9) —$(CH_2)_q$—$R^6$, wherein q and $R^6$ are as defined above, and when q is equal to 1, then $R^6$ is not OH or SH;

(E) $R^7$ and $R^8$ are each independently selected from the group consisting of: H, $C_1$ to $C_6$ alkyl, and $C_3$ to $C_6$ cycloalkyl;

(F) the dotted line (------) represents a double bond that is optionally present when m is 1, and n is not 0, and p is not 0, and when said double bond is present then $R^2$ is absent; and (G) when m is 2, each $R^1$ is the same or different substituent for each m, and each $R^2$ is the same or different substituent for each m, and at least two of the substituents $R^1$ and/or $R^2$ are H.

U.S. Pat. No. 5,633,250 discloses the following compounds:

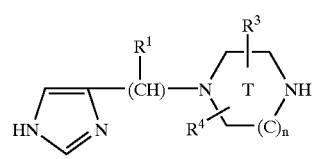

III or a pharmaceutically acceptable salt or solvate thereof, wherein:

(A) n is 1 or 2;

(B) $R^1$ is selected from the group consisting of:

(1) H;

(2) $C_1$ to $C_6$ alkyl;

(3) allyl; and (4) propargyl;

(C) $R^3$ and $R^4$ are independently selected from the group consisting of:

(1) H;

(2) $C_1$ to $C_6$ alkyl;

(3) allyl;

(4) propargyl; and (5) —$(CH_2)_q$—$R^5$ wherein q is an integer of: 1 to 7, and $R^5$ is selected from the group consisting of: phenyl, substituted phenyl, —$OR^6$, —$C(O)OR^6$, —$C(O)R^6$, —$OC(O)R^6$, —$C(O)NR^6R^7$, CN and —$SR^6$ wherein $R^6$ and $R^7$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains 1 to 3 substituents;

(D) $R^6$ and $R^7$ are each independently selected from the group consisting of: H and $C_1$ to $C_6$ alkyl; and (E) $R^3$ and $R^4$ are each independently bound to the same or different carbon atom of ring T.

U.S. Pat. No. 5,578,616 discloses the following compounds:

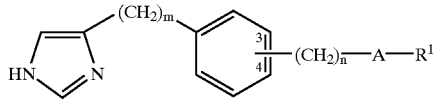

IV wherein:

A is selected from —O—CO—$NR^1$—, —O—CO—, —$NR^1$—CO—$NR^1$—, —$NR^1$—CO—, —$NR^1$—, —O—, —CO—$NR^1$—, —CO—O—, and —$C(:NR^1)$—$NR^1$—;

the groups $R^1$, which may be the same or different when there are 2 or 3 such groups in the molecule shown above, are selected from H, and lower alkyl, aryl, cycloalkyl, heterocyclic and heterocyclyl-alkyl groups, and groups of the formula —$(CH_2)_y$—G, where G is selected from $CO_2R^3$, $COR^3$, $CONR^3R^4$, $OR^3$, $SR^3$, $NR^3R^4$, heteroaryl and phenyl, which phenyl is optionally substituted by halogen, lower alkoxy or polyhaloloweralkyl, and y is an integer from 1 to 3;

$R^2$ is selected from H and halogen atoms, and alkyl, alkenyl, alkynyl and trifluoromethyl groups, and groups of the formula $OR^3$, $SR^3$ and $NR^3R^4$;

$R^3$ and $R^4$ are independently selected from H, and lower alkyl and cycloalkyl groups, or $R^3$ and $R^4$ together with the intervening nitrogen atom can form a saturated ring containing 4 to 6 carbon atoms that can be substituted with 1 or 2 lower alkyl groups;

with the proviso that, when y is 1 and G is $OR^3$, $SR^3$ or $NR^3R^4$, then neither $R^3$ nor $R^4$ is H;

the group —$(CH_2)_n$—A—$R^1$ is at the 3- or 4-position, and the group $R^2$ is at any free position;

m is an integer from 1 to 3; and n is 0 or an integer from 1 to 3;

or a pharmaceutically acceptable acid addition salt thereof;

or a pharmaceutically acceptable salt thereof with a base when G is $CO_2H$;

including a tautomeric form thereof.

U.S. Pat. No. 6,100,279 discloses the following compounds:

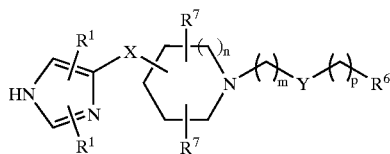

V or pharmaceutically acceptable salts or solvates thereof, wherein:

X is a straight chain alkyl group having 1 to 7 carbon atoms or an alkene or alkyne group with 2 to 4 carbon atoms; wherein said alkyl or alkene groups are optionally substituted with up to two $R^7$ groups;

n is 0, 1 or 2, m and p are 0 to 4;

when m is 0 to 4, Y represents —$SO_2$—; —CS—; —CO—; —$CONR^5$—; —$CO(CH_2)_wO$— (with w being 1 to 4); —COO—; —$CON(OR^5)$—; —$C(NR^5)NR^5$—; —$SO_2NR^5$— or —$CSNR^5$—;

when m is 2 to 4, Y represents all the groups above when m is 0 to 4 and, in addition, Y represents —$CHOR^5$—; —O—; —$NR^5CONR^5$—; —$NR^5CO$—; —$NR^5$—; —$OCONR^5$—; —$NR^5C(NR^5)NR^5$—; —$NR^5CSNR^5$; —$NR^5CS$— or —$NR^5SO_2$—; —$NR^5C(O)O$—; or —$CSNR^5$;

each $R^5$ independently represents H, alkyl or benzyl;

$R^6$ represents aryl, heteroaryl, or a 3- to 7-membered heterocyclic group having one to three heteroatoms in the ring, wherein the heteroatoms are selected from N, S and O, and wherein said $R^6$ group is optionally substituted by one to three substituents as defined below;

when Y is —$SO_2$—, then $R^6$, in addition to the above groups, also represents alkyl having 1 to 7 carbon atoms or a group —$NR^{10}R^{11}$ wherein $R^{10}$ and $R^{11}$ are independently selected from H, alkyl or trihalomethyl;

each $R^1$ is independently H, alkyl or trihalomethyl;

each $R^7$ is independently selected from H, alkyl, trihalomethyl, phenyl or benzyl, wherein said phenyl and benzyl are optionally substituted by one to three substituents independently selected from of alkyl, halogen, trihalomethyl, CN, $NO_2$, $OR^{10}$ or $NR^{10}R^{11}$, wherein $R^{10}$ and $R^{11}$ are as above defined.

U.S. Pat. No. 6,034,251 discloses the following compounds:

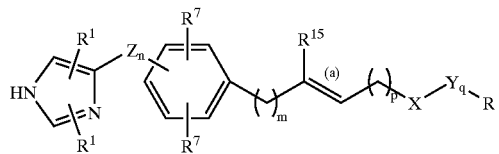

VI or a pharmaceutically acceptable salt or solvate thereof, wherein:

the double bond (a) is E or Z;

each $R^1$ is independently selected from the group consisting of H, lower alkyl, trihalomethyl, phenyl and benzyl;

each $R^7$ is independently selected from the group consisting of H, lower alkyl, halogen, trihalomethyl, $NR^{10}R^{11}$, or a group $OR^{10}$, whereby $R^{10}$ and $R^{11}$ are independently selected from H, lower alkyl or trihalomethyl;

X is —$CONR^5$—; —$SO_2$—, —S—; —CO—; —COO—; —$CN(OR^5)NR^5$—; —$C(NR^5)NR^5$—; —$SONR^5$—; —$SO_2NR^5$— and, provided p is not zero, X may also be —O—; —$NR^5$—; —$NR^5CONR^5$—; —$OCONR^5$—; —O—CO— or —$NR^5CO$—;

Y is $C_1$-$C_3$-alkyl, optionally substituted at any carbon atom of the group by one substituent $R^5$;

Z is $C(R^1)_2$; wherein no more than two $R^1$ groups are other than H;

n is 1 or 2;

m is 0 or 1;

p is 0 or 1;

q is 0 or 1;

R is selected from $C_3$ to $C_7$ cycloalkyl, heterocyclic groups, aryl or heteroaryl, wherein said R groups are optionally substituted with 1–3 substituents;

each $R^5$ independently represents H, lower alkyl or polyhaloloweralkyl; and $R^{15}$ represents H or lower alkyl (e.g., methyl).

U.S. Pat. No. 5,990,147 discloses the following compounds:

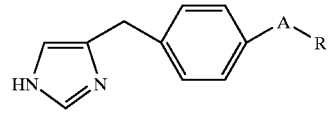

VII or a pharmaceutically acceptable acid addition salt or solvate thereof (or tautomer thereof), wherein:

A is —$CH_2$—NH—CO—NH—; —$CH_2$—O—CO—NH— or —$CH_2CH_2$—CO—NH—$(CH_2)_m$—;

m is 0, 1 or 2;

R is the group

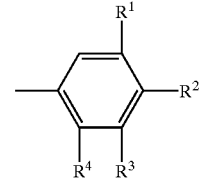

wherein at least two of $R^1$, $R^2$, $R^3$ and $R^4$ are H and the two others are independently selected from H, halogen, $CH_3$, $CF_3$, $OCH_3$, $OCF_3$ or CN; and with the proviso, that when A is —$CH_2$—O—CO—NH— and $R^1$, $R^3$ and $R^4$ are all H, then $R^2$ can not be Cl.

U.S. application Ser. No. 09/978,267 discloses the following compounds:

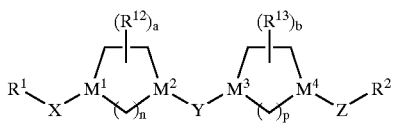

VIII or a pharmaceutically acceptable salt or solvate thereof, wherein:

(1) $R^1$ is selected from aryl, heteroaryl, heterocycloalkyl, alkyl, cycloalkyl, or alkylaryl; wherein said $R^1$ groups are optionally substituted with 1 to 4 substituents independently selected from: halogen, hydroxyl, lower alkoxy, —$CF_3$, $CF_3O$—, —$NR^4R^5$, phenyl, $NO_2$, —$CO_2R^4$, —$CON(R^4)_2$ wherein each $R^4$ is the same or different, —$S(O)_mN(R^{20})_2$ wherein each $R^{20}$ is the same or different H or alkyl group, or —CN; or (2) $R^1$ and X taken together form a group selected from:

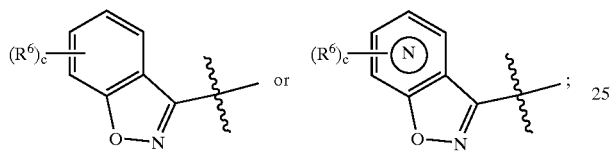

(3) X is selected from: =C(O), =C($NOR^3$), =C($NNR^4R^5$),

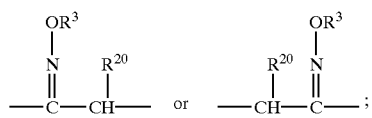

(4) $M^1$ and $M^2$ are independently selected from C or N;
(5) $M^3$ and $M^4$ are independently selected from C or N;
(6) Y is selected from: is —$CH_2$—, =C(O), =C($NOR^{20}$), or =C(S);
(7) Z is a $C_1$–$C_6$ alkyl group;
(8) $R^2$ is a five or six-membered heteroaryl ring, said heteroaryl rings being optionally substituted with 1 to 3 substituents independently selected from: halogen, hydroxyl, lower alkyl, lower alkoxy, —$CF_3$, $CF_3O$—, —$NR^4R^5$, phenyl, —$NO_2$, —$CO_2R^4$, —$CON(R^4)_2$ wherein each $R^4$ is the same or different, —$CH_2NR^4R^5$, —(N)C($NR^4R^5$)$_2$, or —CN;
(9) $R^3$ is selected from H, $C_1$–$C_6$ alkyl, aryl, heteroaryl, heterocycloalkyl, arylalkyl, —$(CH_2)_e$—$C(O)N(R^4)_2$ wherein each $R^4$ is the same or different, —$(CH_2)_e$—$C(O)OR^4$, —$(CH_2)_e$—$C(O)R^{30}$ wherein $R^{30}$ is a heterocycloalkyl group, including

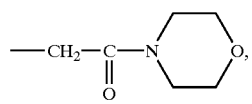

—$CF_3$, or —$CH_2CF_3$;
wherein said aryl, heteroaryl, heterocycloalkyl, and the aryl portion of said arylalkyl are optionally substituted with 1 to 3 substituents selected from: halogen, —OH, —$OCF_3$, —$CF_3$, —CN, —$N(R^{45})_2$, —$CO_2R^{45}$, or —$C(O)N(R^{45})_2$, wherein each $R^{45}$ is independently selected from: H, alkyl, alkylaryl, or alkylaryl wherein said aryl moiety is substituted with 1 to 3 substituents independently selected from —$CF_3$, —OH, halogen, alkyl, —$NO_2$, or —CN;

(10) $R^4$ is selected from: H, $C_1$–$C_6$ alkyl, aryl, alkylaryl, said aryl and alkylaryl groups being optionally substituted with 1 to 3 substituents selected from: halogen, —$CF_3$, —$OCF_3$, —OH, —$N(R^{45})_2$, —$CO_2R^{45}$, —$C(O)N(R^{45})_2$, or —CN; wherein $R^{45}$ is as defined above;

(11) $R^5$ is selected from: H, $C_1$–$C_6$ alkyl, —$C(O)R^4$, —$C(O)_2R^4$, or —$C(O)N(R^4)_2$ wherein each $R^4$ is independently selected, and $R^4$ is as defined above;

(12) or $R^4$ and $R^5$ taken together with the nitrogen atom to which they are bound forms a five or six membered heterocycloalkyl ring;

(13) $R^6$ is selected from: alkyl, aryl, alkylaryl, halogen, hydroxyl, lower alkoxy, —$CF_3$, $CF_3O$—, —$NR^4R^5$, phenyl, —$NO_2$, —$CO_2R^4$, —$CON(R^4)_2$ wherein each $R^4$ is the same or different, or —CN;

(14) $R^{12}$ is selected from: alkyl, hydroxyl, alkoxy, or fluoro;

(15) $R^{13}$ is selected from: alkyl, hydroxyl, alkoxy, or fluoro;

(16) a is 0 to 2;
(17) b is 0 to 2;
(18) c is 0 to 2;
(19) e is 0 to 5;
(20) m is 1 or 2;
(21) n is 1, 2 or 3, with the proviso that when $M^1$ and $M^2$ are both nitrogen, then n is 2 or 3; and
(22) p is 1, 2 or 3, with the proviso that when $M^3$ and $M^4$ are both nitrogen, then p is 2 or 3.

U.S. Provisional Application No. 60/275,417 discloses the following compounds:

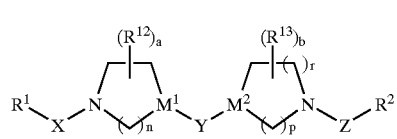

IX or a pharmaceutically acceptable salt or solvate thereof, wherein:

(A) $R^1$ is selected from aryl, heteroaryl, heterocycloalkyl, alkyl, —$C(O)N(R^{48})_2$, cycloalkyl, arylalkyl, heteroarylheteroaryl or a group selected from:

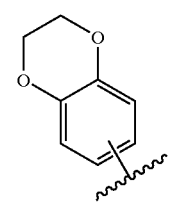

II$^a$

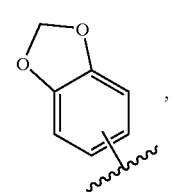

III$^a$

,

-continued

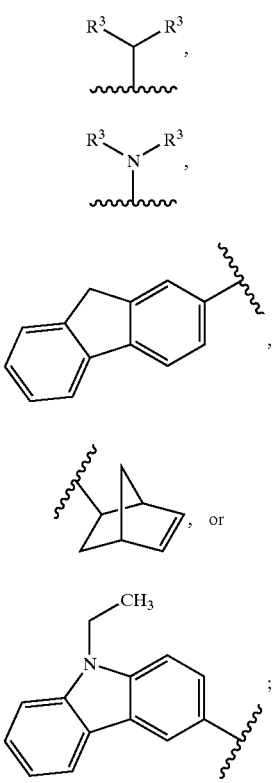

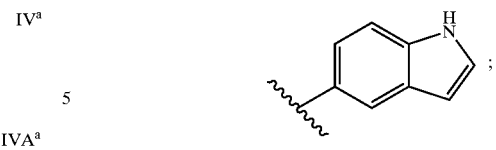

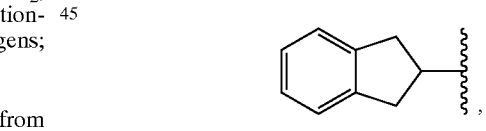

said aryl, heteroaryl, aryl portion of arylalkyl, phenyl ring of formula II$^a$, phenyl ring of formula III$^a$, phenyl rings of formula IVB$^a$, or phenyl rings of formula IVD$^a$ are optionally substituted with 1 to 3 substituents independently selected from halogen; hydroxyl; lower alkoxy; —Oaryl; —SR$^{22}$; —CF$_3$; —OCF$_3$; —OCHF$_2$; —NR$^4$R$^5$; phenyl; NO$_2$; —CO$_2$R$^4$; —CON(R$^4$)$_2$, wherein each R$^4$ is the same or different; —S(O)$_2$R$^{22}$; —S(O)$_2$N(R$^{20}$)$_2$, wherein each R$^{20}$ is the same or different; —N(R$^{24}$)S(O)$_2$R$^{22}$; —CN; —CH$_2$OH; —OCH$_2$CH$_2$OR$^{22}$; alkyl; substituted phenyl wherein said phenyl has 1 to 3 substituents independently selected from alkyl, halogen, —CN, —NO$_2$, —OCHF$_2$, —Oalkyl; —Oalkylaryl wherein said aryl group is optionally substituted with 1 to 3 independently selected halogens; or phenyl;

(B) X is selected from alkyl or —S(O)$_2$—;

(C) Y represents a single bond; or Y is selected from —C(O)—, —C(S)—, —(CH$_2$)$_q$—, or —NR$^4$C(O)—; with the provisos that when M$^1$ is N, then Y is not —NR$^4$C(O)—; and when Y is a bond, then M$^1$ and M$^2$ are both carbon;

(D) M$^1$ and M$^2$ are independently selected from C or N;

(E) Z is selected from: C$_1$–C$_6$ alkyl, —SO$_2$—, —C(O)— or —C(O)NR$^4$—;

(F) R$^2$ is selected from: a six-membered heteroaryl ring having 1 or 2 heteroatoms independently selected from N or N—O, with the remaining ring atoms being carbon; a five-membered heteroaryl ring having 1 to 3 heteroatoms selected from nitrogen, oxygen, or sulfur with the remaining ring atoms being carbon; an alkyl group; an aryl group wherein said substituted phenyl is substituted with 1 to 3 substituents independently selected from halogen, —Oalkyl, —OCF$_3$, —CF$_3$, —CN, —NO$_2$, —NHC(O)CH$_3$, or —O(CH$_2$)$_q$N(R$^{10A}$)$_2$; —N(R$^{11A}$)$_2$ wherein each R$^{11A}$ is independently selected from H, alkyl or aryl; a group of the formula or a heteroarylheteroaryl group;

said five membered heteroaryl ring or six-membered heteroaryl ring is optionally substituted with 1 to 3 substituents selected from halogen; hydroxyl; lower alkyl; lower alkoxy; —CF$_3$; —NR$^4$R$^5$; phenyl; —NO$_2$; —C(O)N(R$^4$)$_2$ (wherein each R$^4$ is the same or different); —C(O)$_2$R$^4$; or phenyl substituted with 1 to 3 substituents independently selected from: halogen, —Oalkyl, —OCF$_3$, —CF$_3$, —CN, —NO$_2$ or —O(CH$_2$)$_q$N(R$^{10A}$)$_2$;

(G) R$^3$ is is selected from aryl; heteroaryl; heterocycloalkyl; alkyl; or cycloalkyl; wherein said aryl or heteroaryl R$^3$ groups is optionally substituted with 1 to 3 substituents independently selected from halogen; hydroxyl; lower alkoxy; —Oaryl; —SR$^{22}$; —CF$_3$; —OCF$_3$; —OCHF$_2$; —NR$^4$R$^5$; phenyl; —NO$_2$; —CO$_2$R$^4$; —CON(R$^4$)$_2$ wherein each R$^4$ is the same or different; —S(O)$_2$R$^{22}$; —S(O)$_2$N(R$^{20}$)$_2$ wherein each R$^{20}$ is the same or different; —N(R$^{24}$)S(O)$_2$R$^{22}$; —CN; —CH$_2$OH; —OCH$_2$CH$_2$OR$^{22}$; or alkyl;

(H) R$^4$ is selected from hydrogen; C$_1$–C$_6$ alkyl; cycloalkyl; cycloalkylalkyl; heterocycloalkylalky; bridged bicyclic cycloalkyl ring; aryl having a fused heterocycloalkyl ring bound to said aryl ring; aryl; arylalkyl; alkylaryl; —(CH$_2$)$_d$CH(R$^{12A}$)$_2$ wherein d is 1 to 3, and each R$^{12A}$ is independently selected from phenyl or substituted phenyl, said substituted phenyl being substituted with 1 to 3 substituents independently selected from: halogen, —Oalkyl, —OCF$_3$, —CF$_3$, —CN, or —NO$_2$; heterocycloalkylheteroaryl; or —(C$_1$ to C$_6$)alkylene—O—R$^{22}$;

wherein the aryl R$^4$ group, the aryl portion of the arylalkyl R$^4$ group, or the aryl portion of the alkylaryl R$^4$ group is optionally substituted with 1 to 3 substituents independently selected from halogen; hydroxyl; lower alkyl; lower alkoxy; —CF$_3$; —N(R$^{20}$)(R$^{24}$); phenyl; —NO$_2$; —C(O)N(R$^{20}$)$_2$ (wherein each R$^{20}$ is the same or different); —C(O)R$^{22}$; —(CH$_2$)$_k$-cycloalkyl; —(CH$_2$)$_q$-aryl; or —(CH$_2$)$_m$—OR$^{22}$;

(I) each R$^{4B}$ is independently selected from: H, heteroaryl, alkyl, alkenyl, a group of the formula arylalkyl, or arylalkyl wherein the aryl moiety is substitued with 1–3 substituents independently selected from: halogen;

(J) R$^5$ is selected from: hydrogen, C$_1$–C$_6$ alkyl, —C(O)R$^{20}$, —C(O)$_2$R$^{20}$, —C(O)N(R$^{20}$)$_2$ (wherein each R$^{20}$ is the same or different);

(K) each R$^{10A}$ is independently selected from H or C$_1$ to C$_6$ alkyl, or each R$^{10A}$, taken together with the nitrogen atom to which they are bound, forms a 4 to 7 membered heterocycloalkyl ring;

(L) R$^{12}$ is selected from alkyl, hydroxyl, alkoxy, or fluoro, provided that when R$^{12}$ is hydroxy or fluoro then R$^{12}$ is not bound to a carbon adjacent to a nitrogen; or R$^{12}$ forms an alkyl bridge from one ring carbon to another ring carbon;

(M) R$^{13}$ is selected from alkyl, hydroxyl, alkoxy, or fluoro, provided that when R$^{13}$ is hydroxy or fluoro then R$^{13}$ is not bound to a carbon adjacent to a nitrogen; or R$^{13}$ forms an alkyl bridge from one ring carbon to another ring carbon;

(N) $R^{20}$ is selected from hydrogen, alkyl, or aryl, wherein said aryl group is optionally substituted with from 1 to 3 groups independently selected from: halogen, —$CF_3$, —$OCF_3$, hydroxyl, or methoxy; or when two $R^{20}$ groups are present, said two $R^{20}$ groups taken together with the nitrogen to which they are bound form a five or six membered heterocyclic ring;

(O) $R^{22}$ is selected from: heterocycloalkyl, alkyl or aryl, wherein said aryl group is optionally substituted with 1 to 3 groups independently selected from halogen, —$CF_3$, —$OCF_3$, hydroxyl, or methoxy;

(P) $R^{24}$ is selected from: hydrogen, alkyl, —$SO_2R^{22}$, or aryl, wherein said aryl group is optionally substituted with 1 to 3 groups independently selected from halogen, —$CF_3$, —$OCF_3$, hydroxyl, or methoxy;

(Q) a is 0 to 2;

(R) b is 0 to 2;

(S) k is 1 to 5;

(T) m is 2 to 5;

(U) n is 1, 2 or 3 with the proviso that when $M^1$ is N, then n is not 1;

(V) p is 1, 2 or 3 with the proviso that when $M^2$ is N, then p is not 1;

(W) q is 1 to 5; and (X) r is 1, 2, or 3 with the proviso that when r is 2 or 3, $M^2$ is C and p is 1.

Other $H_3$ receptor antagonists can be identified by the test method described below.

Preferred $H_3$ antagonists are clobenpropit, impromidine, GT-2331, GR-175737, UCL-1199, and those disclosed in U.S. Pat. No. 5,990,147, U.S. application Ser. No. 09/978,267 and U.S. Provisional Application 60/275,417.

Muscarinic antagonists, in particular those having $m_2$ activity, are disclosed in several U.S. patents. U.S. Pat. No. 5,883,096 and a divisional thereof, U.S. Pat. No. 6,037,352, disclose the following compounds:

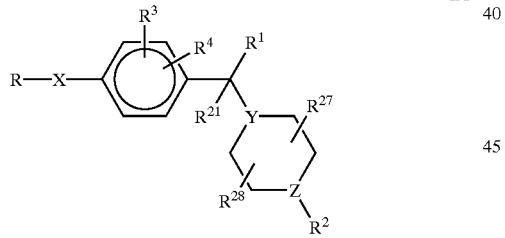

IA including all isomers and pharmaceutically acceptable salts, esters, and solvates thereof, wherein one of Y and Z is N and the other is N, CH, or C-alkyl;

X is —O—, —S—, —SO—, —$SO_2$—, —$NR^6$—, —CO—, —$CH_2$—, —CS—, —$C(OR^5)_2$—, —$C(SR^5)_2$—, —$CONR^{20}$—, —$C(alkyl)_2$—, —C(H)(alkyl)—, —$NR^{20}SO_2$—, —$NR^{20}CO$—,

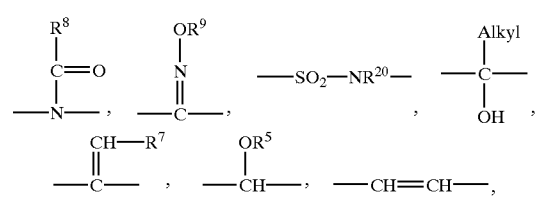

R is

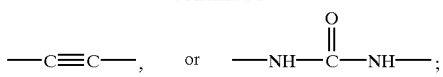

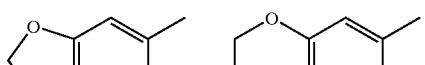

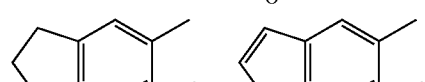

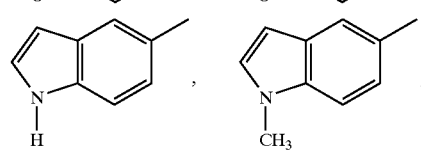

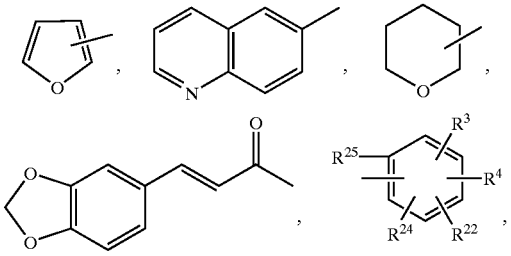

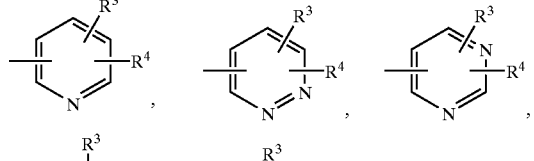

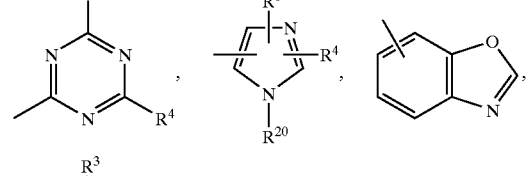

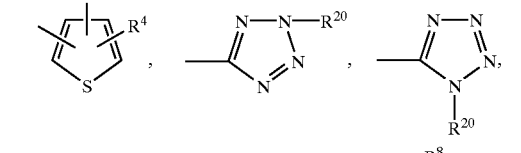

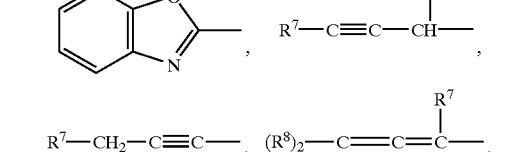

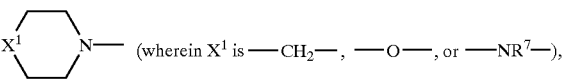

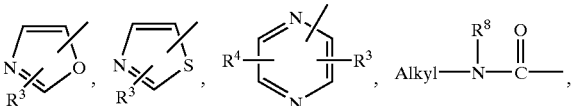

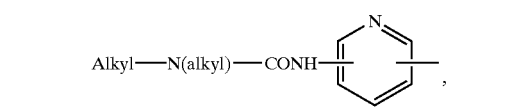

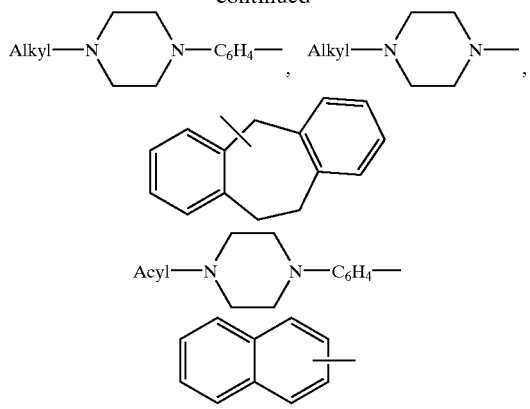

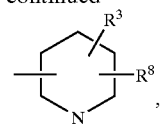

hydrogen, acyl, alkyl, alkenyl, cycloalkyl, cycloalkyl substituted with up to two alkyl groups, cycloalkenyl, bicycloalkyl, arylalkenyl, benzyl, benzyl substituted with up to three independently selected $R^3$ groups, cycloalkylalkyl, polyhaloacyl, benzyloxyalkyl, hydroxyC$_2$–C$_{20}$alkyl, alkenylcarbonyl, alkylarylsulfonyl, alkoxycarbonyl-aminoacyl, alkylsulfonyl, or arylsulfonyl, additionally, when X is —CH$_2$—, R may also be —OH; in further addition, when X is not N, R may also be hydroxymethyl, in further addition, R and X may combine to form the group Prot-(NOAA)$_r$—NH— wherein r is an integer of 1 to 4, Prot is a nitrogen protecting group and when r is 1, NOAA is a naturally occuring amino acid or an enantiomer thereof, or when r is 2 to 4, each NOAA is a peptide of an independently selected naturally occuring amino acid or an enantiomer thereof;

$R^1$ and $R^{21}$ are independently selected from the group consisting of alkyl, alkenyl, cycloalkyl, cycloalkenyl, bicycloalkyl, alkynyl, cyano, aminoalkyl, alkoxycarbonyl, aminocarbonyl, hydroxyguanidino, alkoxycarbonylalkyl, phenyl alkyl, alkylcarbonlyoxyalkyl,

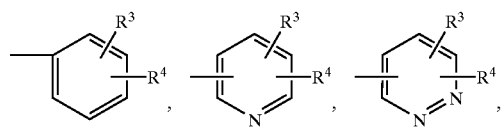

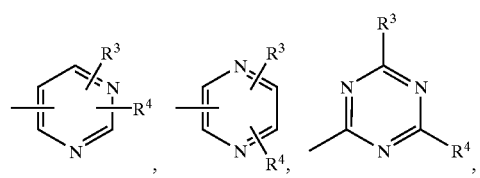

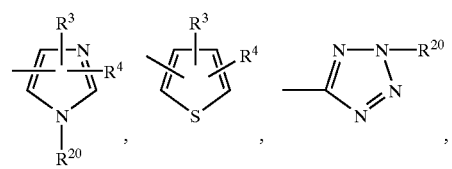

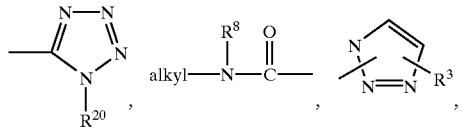

H, —OH, (provided $R^1$ and $R^{21}$ are both not —OH and Y is not N), formyl, —CO alkyl, —COacyl, —COaryl, and hydroxyalkyl; additionally $R^1$ and $R^{21}$ together may form the group =CH$_2$, =N—OR$^5$, =N—CN, =N—N(R$^5$)$_2$, =CH-Alkyl, alkylene, =O,

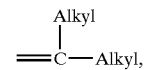

50 C(halo)$_2$, in further addition, $R^1$ and $R^{21}$ together with the carbon atom to which they are attached may form the group

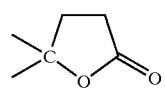

or $R^1$ and $R^{21}$ together with the carbon atom to which they are attached may form a saturated heterocyclic ring containing 3 to 7 carbon atoms and one group selected from S, O, and NH;

$R^2$ is H, alkyl, alkenyl, cycloalkyl, cycloalkyl substituted with 1 to 3 independently selected $R^3$ groups, cycloalkenyl, hydroxyC$_2$–C$_{20}$alkyl, alkynyl, alkylamide, cycloalkylalkyl, hydroxyarylalkyl, bicycloalkyl, alkynyl, acylaminoalkyl, arylalkyl, hydroxyalkoxyalkyl, azabicyclo, alkylcarbonyl, alkoxyalkyl, aminocarbonylalkyl, alkoxycarbonyl-aminoalkyl, alkoxycarbonylamino(alkyl)alkyl; alkyl-carbonyloxyalkyl, arylhydroxyalkyl, alkylcarbonylamino(alkyl)alkyl, dialkylamino,

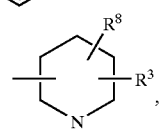

(wherein q is an integer of 0 to 2)

wherein n is 1–3

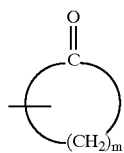

wherein m is an integer of 4 to 7,

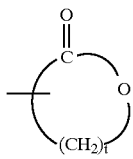

wherein t is an integer of 3 to 5,

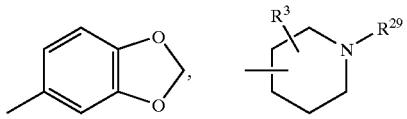

(wherein $R^{29}$ is H, alkyl, acyl, alkoxycarbonyl, aminocarbonyl, alkylaminocarbonyl, dialkylaminocarbonyl, alkylsulfonyl, arylsulfonyl),

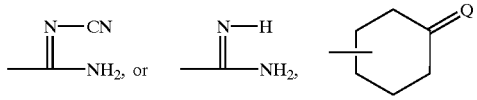

(wherein Q is O, NOH, or NO-alkyl), or when Z is —CH—, $R^2$ may also be alkoxycarbonyl, hydroxymethyl, —N($R^8$)$_2$;

$R^3$, $R^4$, $R^{22}$, $R^{24}$, and $R^{25}$ are independently selected from the group consisting of H, halo, alkoxy, benzyloxy, benzyloxy substituted by nitro or aminoalkyl, haloalkyl, polyhaloalkyl, nitro, cyano, sulfonyl, hydroxy, amino, alkylamino, formyl, alkylthio, polyhaloalkoxy, acyloxy, trialkylsilyl, alkylsulfonyl, arylsulfonyl, acyl, alkoxycarbonyl alkylsulfinyl; —OCONH$_2$, —OCONH-alkyl, —OCON(alkyl)$_2$, —NHCOO-alkyl, —NHCO-alkyl, phenyl, hydroxyalkyl, or morpholino;

each $R^5$ and $R^6$ is independently selected from the group consisting of H and alkyl, provided that when X is C(OR$^5$)$_2$ or C(SR$^5$)$_2$, both $R^5$ groups cannot be H, and in addition, when X is C(OR$^5$)$_2$ or C(SR$^5$)$_2$, the two $R^5$ groups in X may be joined to form —(CH$_2$)$_p$— wherein p is an integer of 2 to 4;

$R^7$ is independently selected from the group consisting of H, alkyl, arylalkyl, cycloalkyl, aryl and aryl substituted with $R^3$ and $R^4$ as defined herein;

each $R^8$ is independently selected from the group consisting of H, hydroxyalkyl, or alkyl or two $R^8$ groups may be joined to form an alkylene group;

$R^9$ is H, alkyl, or acyl;

$R^{20}$ is H, phenyl or alkyl; and $R^{27}$ and $R^{28}$ are independently selected from the group consisting of H, alkyl, hydroxyalkyl, arylalkyl, aminoalkyl, haloalkyl, thioalkyl, alkylthioalkyl, carboxyalkyl, imidazolylalkyl, and indolylalkyl, additionally $R^{27}$ and $R^{28}$ may combine to form an alkylene group.

U.S. Pat. No. 5,889,006 and a divisional thereof, U.S. Pat. No. 6,043,255, disclose compounds of the formula

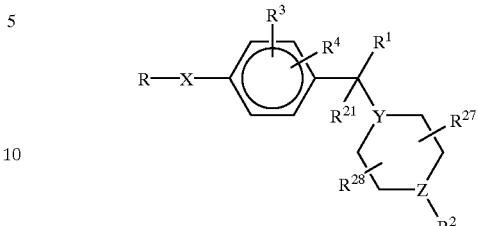

IA-1 wherein R, $R^1$, $R^3$, $R^4$, $R^{21}$, $R^{27}$, and $R^{28}$ are as described in U.S. Pat. No. 5,883,096, but wherein $R^2$ is:

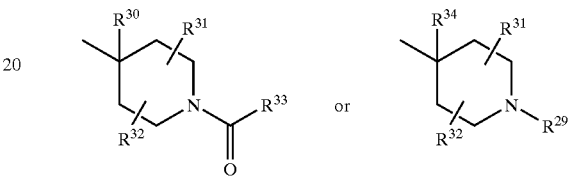

wherein $R^{29}$ is H, alkyl, —CO-alkyl, alkoxycarbonyl, aminocarbonyl, aryloxycarbonyl alkylaminocarbonyl, dialkylaminocarbonyl, alkylsulfonyl, or arysulfonyl;

$R^{30}$ is H, alkyl, aryl, cycloalkyl, hydroxyalkyl, aminoalkyl, —COOR$^{20}$, —CON(R$^{20}$)$_2$ or cyano;

$R^{31}$ and $R^{32}$ are the same as $R^{30}$ and in addition, two $R^{30}$, $R^{31}$ and $R^{32}$ groups may form the group —(CH$_2$)$_r$— (wherein r is 1 to 6), in further addition, $R^{31}$ and $R^{32}$ can also be hydroxy, —N(R$^{20}$)$_2$, —O-acyl, —N(R$^{20}$)acyl, —OCOOR$^{20}$, or —OCON(R$^{20}$)$_2$;

$R^{33}$ is aryl or heteroaryl, with the proviso that when $R^{33}$ is heteroaryl, the CO—R$^{33}$ bond is to a carbon atom in the $R^{33}$ group; and $R^{34}$ is alkyl, cycloalkyl or aryl and in addition $R^{34}$ may also be H when $R^1$ and $R^{21}$ together with the carbon atom to which they are attached form a saturated heterocyclic ring containing 3 to 7 carbon atoms and two groups independently selected from S, O, and N—R$^{20}$.

U.S. Pat. No. 5,952,349 discloses the following compounds:

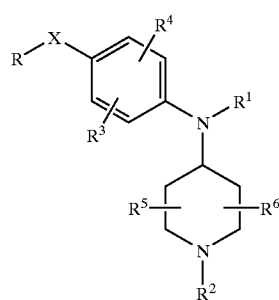

IIA or an isomer, pharmaceutically acceptable salt, ester or solvate thereof, wherein X is a bond, —O—, —S—, —SO—, —SO$_2$—, —CO—, —C(OR$^7$)$_2$—, —CH$_2$—O—, —O—CH$_2$—, —CH=CH—, —CH$_2$—, —CH(C$_1$-C$_6$ alkyl)—, —C(C$_1$-C$_6$ alkyl)$_2$—, —CONR$^{17}$—, —NR$^{17}$CO—, —SO$_2$NR$^{17}$— or —NR$^{17}$SO$_2$—;

R is C$_3$–C$_6$ cycloalkyl,

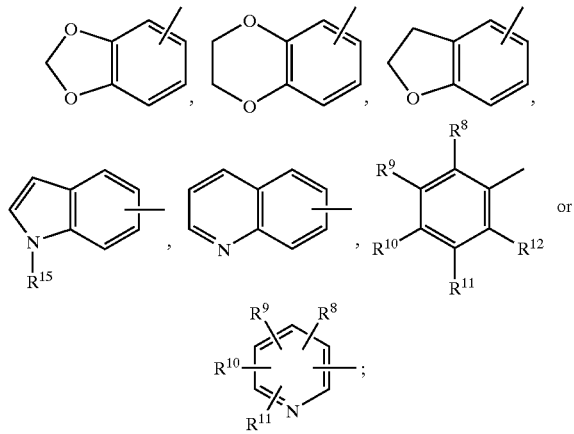

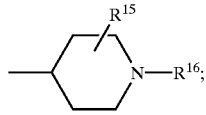

R$^1$ is H, —CN, —CF$_3$, C$_1$–C$_6$ alkyl, C$_3$–C$_6$ cycloalkyl, C$_3$–C$_6$ cycloalkenyl, C$_3$–C$_6$ alkenyl, —COR$^{15}$, —COO(C$_1$–C$_6$ alkyl), —COO(aryl), —COO(heteroaryl), —COO((C$_1$–C$_6$ alkyl)aryl), —COO((C$_1$–C$_6$ alkyl)heteroaryl), —(C$_1$–C$_6$ alkyl)aryl, —(C$_1$–C$_6$ alkyl)heteroaryl or —CON(R$^{13}$)$_2$;

R$^2$ is C$_3$–C$_6$ cycloalkyl, C$_3$–C$_6$ cycloalkenyl, t-butoxycarbonyl or

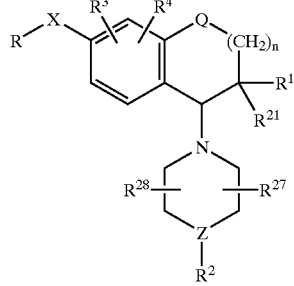

R$^3$ and R$^4$ are independently selected from the group consisting of H, halo, —CF$_3$, C$_1$–C$_6$ alkyl, C$_1$–C$_6$ alkoxy and —OH;

R$^5$ and R$^6$ are independently selected from the group consisting of H, C$_1$–C$_6$ alkyl, —CF$_3$, C$_1$–C$_6$ alkoxy, —OH, C$_1$–C$_6$ alkylcarbonyl, C$_1$–C$_6$ alkoxycarbonyl, R$^{13}$CONH—, R$^{14}$OCONH—, R$^{13}$NHCONH— and NH$_2$CONR$^{13}$—;

R$^7$ is independently selected from the group consisting of H and alkyl, provided that both R$^7$ groups are not H; or the two R$^7$ groups may be joined to form —(CH$_2$)$_p$— wherein p is an integer of 2 to 4;

R$^8$, R$^9$, R$^{10}$, R$^{11}$ and R$^{12}$ are independently selected from the group consisting of H, halo, C$_1$–C$_6$ alkyl, C$_1$–C$_6$ alkoxy, benzyloxy, benzyloxy substituted by —NO$_2$ or —N(R$^{14}$), halo C$_1$–C$_6$ alkyl, polyhalo C$_1$–C$_6$ alkyl, —NO$_2$, —CN, —SO$_2$, —OH, —NH$_2$, —N(R$^{14}$)$_2$, —HCO, polyhalo C$_1$–C$_6$ alkoxy, acyloxy, (C$_1$–C$_4$ alkyl)$_3$Si—, (C$_1$–C$_6$ alkyl)SO$_{0-2}$, arylsulfonyl, heteroaryl-sulfonyl, acyl, (C$_1$–C$_6$ alkoxy)CO—, —OCON(R$^{14}$)$_2$, —NHCOO—(C$_1$–C$_6$)alkyl, —NHCO—(C$_1$–C$_6$ alkyl), phenyl, hydroxy(C$_1$–C$_6$ alkyl) or morpholino;

R$^{13}$ is independently selected from the group consisting of H, C$_1$–C$_6$ alkyl, C$_3$–C$_6$ cycloalkyl, —(C$_1$–C$_6$ alkyl)COOR$^{15}$, aryl, heteroaryl, —(C$_1$–C$_6$ alkyl)aryl, —(C$_1$–C$_6$ alkyl)heteroaryl and adamantyl;

R$^{14}$ is independently selected from the group consisting of H and C$_1$–C$_6$ alkyl;

R$^{15}$ is H, C$_1$–C$_{20}$ alkyl, C$_1$–C$_6$ cycloalkyl, aryl or heteroaryl;

R$^{16}$ is H, C$_1$–C$_6$ alkyl, —COR$^{15}$, C$_1$–C$_6$ alkoxycarbonyl, (R$^{14}$)$_2$NCO— or —SO$_{1-2}$—R$^{15}$; and R$^{17}$ is H, C$_1$–C$_6$ alkyl, aryl or heteroaryl.

U.S. Pat. No. 5,935,958 discloses the following compounds:

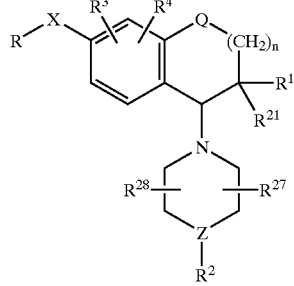

IIIA including all stereoisomers and pharmaceutically acceptable salts, esters, and solvates thereof, wherein:

Z is N, CH or C-alkyl;

X is —O—, —S—, —SO—, —SO$_2$—, —CO—, —CH$_2$—, —CONR$^{20}$—, —NR$^{20}$—SO$_2$—, —NR$^{20}$CO—, or —SO$_2$—NR$^{20}$—;

Q is —O—, —S—, —SO—, —SO$_2$—, or —CH$_2$—;

R is

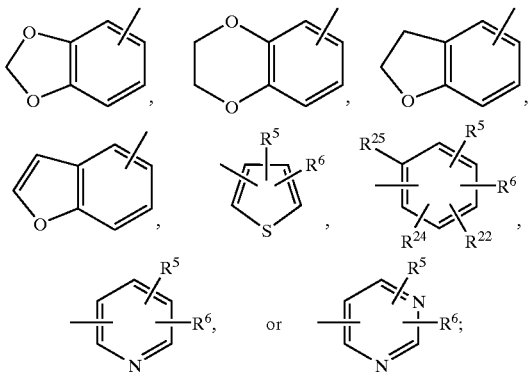

R$^1$ and R$^{21}$ are independently selected from the group consisting of hydrogen, alkyl, alkenyl, cycloalkyl, cycloalkenyl, cycloalkylalkyl, cycloalkenylalkyl, phenylalkyl, and hydroxyalkyl;

R$^2$ is cycloalkyl, cycloalkyl substituted with 1 to 3 independently selected R$^3$ groups, cycloalkenyl, cycloalkylalkyl,

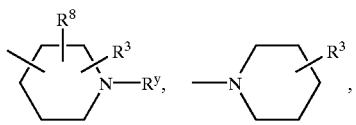

(wherein R$^y$ is H, alkyl, alkenyl, SO$_2$R$^z$ or COR$^z$ wherein R$^z$ is alkyl, alkenyl, aryl, heteroaryl, or cycloalkyl), with the proviso that R$^2$ is R$^3$-substituted-1-piperidinyl only when Z is CH or C-alkyl; or, when Z is CH, R$^2$ may also be alkoxycarbonyl, —N(R$^9$)(hydroxyalkyl) wherein R$^9$ is H, hydroxyalkyl, or alkyl, or —N(R$^9$)$_2$ wherein the two R$^9$ groups may be joined to form an alkylene group;

R$^3$, R$^4$, R$^5$, R$^6$, R$^{22}$, R$^{24}$, and R$^{25}$ are independently selected from the group consisting of H, alkyl, halo, alkoxy, benzyloxy, benzyloxy substituted by nitro or aminoalkyl, polyhaloalkyl, nitro, sulfonyl, hydroxy, amino, alkylamino, formyl, alkylthio, acyloxy, alkylsulfonyl, arylsulfonyl, acyl, alkoxycarbonyl, alkylsulfinyl, —OCONH$_2$, —OCONH-alkyl, —OCON(alkyl)$_2$, —NHCOO-alkyl, —NHCO-alkyl, phenyl, hydroxyalkyl, and 1-morpholinyl;

$R^8$ is hydrogen, lower alkyl or cyclopropyl;

$R^{20}$ is H, phenyl or alkyl;

$R^{27}$ and $R^{28}$ are independently selected from the group consisting of H, alkyl, hydroxyalkyl, alkoxyalkyl, arylalkyl, mercaptoalkyl, alkylthioalkyl, and carboxyalkyl, and additionally $R^{27}$ and $R^{28}$ may be joined to form an alkylene group; and n is 0 or an integer from 1 to 3.

U.S. Pat. No. 6,066,636 discloses the following compounds:

IVA including all stereoisomers and pharmaceutically acceptable salts and solvates thereof, wherein one of Y and Z is —N— and the other is —N— or —CH—;

X is —O—, —S—, —SO—, —SO$_2$— or —CH$_2$—;

Q is

R is (C$_1$–C$_{20}$)alkyl, (C$_3$–C$_{12}$)cycloalkyl, aryl, R$^8$-aryl or heteroaryl;

$R^1$, $R^2$ and $R^3$ are independently selected from the group consisting of H and (C$_1$–C$_{20}$)alkyl;

$R^4$ is (C$_1$–C$_{20}$)alkyl, (C$_3$–C$_{12}$)cyclolalkyl or $R^5$ is H, (C$_1$–C$_{20}$)alkyl, —C(O)(C$_1$–C$_{20}$)alkyl, R$^9$-arylcarbonyl, —SO$_2$(C$_1$–C$_{20}$)alkyl, R$^9$-arylsulfonyl —C(O)O(C$_1$–C$_{20}$)alkyl, R$^9$-aryloxy-carbonyl, —C(O)NH—(C$_1$–C$_{20}$)alkyl or R$^9$-arylaminocarbonyl;

$R^6$ is H or (C$_1$–C$_{20}$)alkyl;

$R^7$ is H, (C$_1$–C$_{20}$)alkyl, hydroxy(C$_1$–C$_{20}$)alkyl or (C$_1$–C$_{20}$)-alkoxy(C$_1$–C$_{20}$)alkyl;

$R^8$ is 1–3 substituents independently selected from the group consisting of H, (C$_1$–C$_{20}$)alkyl, halogen, hydroxy, (C$_1$–C$_{20}$)alkoxy or hydroxy(C$_1$–C$_{20}$)alkyl, or two adjacent $R^8$ groups may be joined to form a (C$_1$–C$_2$)alkylenedioxy group; and $R^9$ is 1–3 substituents independently selected from the group consisting of H, (C$_1$–C$_{20}$)alkyl, halogen, amino or (C$_1$–C$_{20}$)alkylamino.

U.S. Pat. No. 5,977,138 discloses the following compounds:

VA or an isomer, pharmaceutically acceptable salt, ester or solvate thereof, wherein X is a bond, —O—, —S—, —SO—, —SO$_2$—, —CO—, —C(OR$^7$)$_2$—, —CH$_2$—O—, —O—CH$_2$—, —CH═CH—, —CH$_2$—, —CH(C$_1$–C$_6$ alkyl)—, —C(C$_1$–C$_6$ alkyl)$_2$—, —CONR$^{17}$—, —NR$^{17}$CO—, —O—C(O)NR$^{17}$—, —NR$^{17}$C(O)—O—, —SO$_2$NR$^{17}$— or —NR$^{17}$SO$_2$—;

R is C$_3$–C$_6$ cycloalkyl, n is 1, 2 or 3;

$R^2$ is H, C$_2$–C$_7$ alkyl, C$_3$–C$_7$ cycloalkyl, C$_3$–C$_7$ cycloalkyl substituted by 1 to 4 groups independently selected from R$^{18}$, C$_3$–C$_6$ cycloalkenyl, t-butoxycarbonyl or $R^3$ and $R^4$ are independently selected from the group consisting of H, halo, —CF$_3$, C$_1$–C$_6$ alkyl, C$_1$–C$_6$ alkoxy and —OH;

$R^5$ and $R^6$ are independently selected from the group consisting of H, C$_1$–C$_6$ alkyl, —CF$_3$, C$_1$–C$_6$ alkoxy, —OH, C$_1$–C$_6$ alkylcarbonyl, C$_1$–C$_6$ alkoxycarbonyl, R$^{13}$CONH—, (R$^{13}$)$_2$NCO—, R$^{13}$OCONH—, R$^{13}$NHCONH— and NH$_2$CONR$^{13}$—;

$R^7$ is independently selected from the group consisting of C$_1$–C$_6$ alkyl; or the two R$^7$ groups may be joined to form —(C(R$^{14}$)$_2$)$_p$— wherein p is an integer from 2–4;

$R^8$, $R^9$, $R^{10}$, $R^{11}$ and $R^{12}$ are independently selected from the group consisting of H, halo, $C_1$–$C_6$ alkyl, $C_1$–$C_6$ alkoxy, benzyloxy, benzyloxy substituted by —$NO_2$ or —$N(R^{14})$, halo $C_1$–$C_6$ alkyl, polyhalo $C_1$–$C_6$ alkyl, —$NO_2$, —CN, —$SO_2$, —OH, —$NH_2$, —$N(R^{14})_2$, —CHO, polyhalo $C_1$–$C_6$ alkoxy, acyloxy, ($C_1$–$C_4$ alkyl)$_3$Si—, ($C_1$–$C_6$ alkyl)$SO_{0-2}$, arylsulfonyl, heteroaryl-sulfonyl, acyl, ($C_1$–$C_6$ alkoxy)CO—, —$OCON(R^{14})_2$, —NHCOO—($C_1$–$C_6$)alkyl, —NHCO—($C_1$–$C_6$ alkyl), phenyl, hydroxy($C_1$–$C_6$ alkyl) or morpholino;

$R^{13}$ is independently selected from the group consisting of H, $C_1$–$C_6$ alkyl, $C_3$–$C_6$ cycloalkyl, —($C_1$–$C_6$ alkyl)$COOR^{15}$, aryl, heteroaryl, —($C_1$–$C_6$ alkyl)aryl, —($C_1$–$C_6$ alkyl)heteroaryl and adamantyl;

$R^{14}$ is independently selected from the group consisting of H and $C_1$–$C_6$ alkyl;

$R^{15}$ is independently selected from the group consisting of H, $C_1$–$C_{20}$ alkyl, $C_3$–$C_6$ cycloalkyl, aryl substituted by 1 to 3 groups independently selected from $R^3$ and heteroaryl substituted by 1 to 3 groups independently selected from $R^3$;

$R^{16}$ is H, $C_1$–$C_6$ alkyl, —$COR^{20}$, $C_1$–$C_6$ alkoxycarbonyl, —$CON(R^{14})_2$, —$CONH(R^3$-aryl), —$SO_{1-2}$—$R^{15}$, —$SO_{1-2}$—$(CH_2)_m$—$R^{21}$, —$SON(R^{14})_2$, —$COSR^{14}$ or

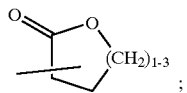
;

$R^{17}$ is H, $C_1$–$C_6$ alkyl, aryl or heteroaryl;

$R^{18}$ is independently selected from the group consisting of halo, —$CF_3$, $C_1$–$C_6$ alkyl, $C_1$–$C_6$ alkoxy, —OH, =O, —$CON(R^{14})_2$ and —$N(R^{14})COR^{15}$;

$R^{19}$ is H, —OH, $C_1$–$C_{20}$ alkyl, $C_3$–$C_6$ cycloalkyl, aryl substituted by 1 to 3 groups independently selected from $R^3$ or heteroaryl substituted by 1 to 3 groups independently selected from $R^3$;

$R^{20}$ is H, $C_1$–$C_{20}$ alkyl, $C_1$–$C_6$ alkoxy($C_1$–$C_6$)alkyl, $C_3$–$C_6$ cycloalkyl, aryl, aryl($C_1$–$C_6$ alkyl)—, aryloxy, aryloxy($C_1$–$C_6$ alkyl)—, tetrahydrofuranyl or heteroaryl, wherein the aryl or heteroaryl group is substituted by 1 to 3 groups independently selected from $R^3$;

m is 0 to 3; and $R^{21}$ is $C_7$–$C_{10}$ bridged cycloalkyl or $C_7$–$C_{10}$ bridged cycloalkyl wherein the cycloalkyl portion is substituted by 1 or 2 substituents selected from the group consisting of $C_1$–$C_6$ alkyl or =O.

A genus of selective $m_2$ muscarinic antagonists, disclosed in U.S. Pat. No. 6,294,554 B1, has the following structural formula:

VIA

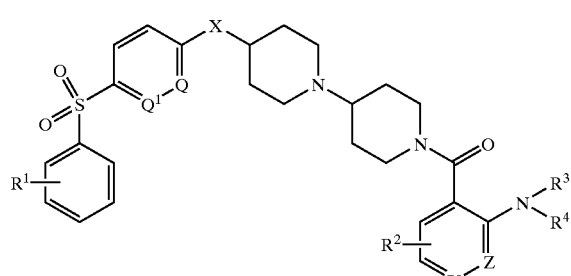

or a pharmaceutically acceptable salt, ester or solvate thereof, wherein

Q and $Q^1$ are each —CH=, or one of Q and $Q^1$ is —CH= and the other is —N=;

X is —$CH_2$— or

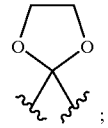
;

Y and Z are independently selected from the group consisting of —$C(R^5)$=, or one of Y and Z is —$C(R^5)$= and the other is —N=;

$R^1$ is 1 to 3 substituent independently selected from the group consisting of H, halogen and ($C_1$–$C_6$)alkoxy;

$R^2$ and $R^5$ are independently 1 to 3 substituents independently selected from the group consisting of H, halogen, ($C_1$–$C_6$)alkyl and ($C_1$–$C_6$)alkoxy; and $R^3$ and $R^4$ are independently selected from the group consisting of H and ($C_1$–$C_6$)alkyl.

Of those compounds, preferred are compounds wherein both Y and Z are —$C(R^5)$=, and wherein $R^5$ is preferably H, methyl or halogen. Also preferred are compounds wherein Y is —CH=, Z is —N= and $R^2$ is hydrogen. $R^1$ is preferably halogen, more preferably chloro, or methoxy, and in particular, $R^1$ is 3-chloro or 4-methoxy. Q and $Q^1$ are preferably each —CH=. Preferred $R^2$ substituents are Cl, F and methyl, with 3-methyl being more preferred. $R^3$ and $R^4$ are preferably each H.

U.S. Provisional Application No. 60/257,853, filed Dec. 22, 2000 discloses compounds having the following structure:

VIIA

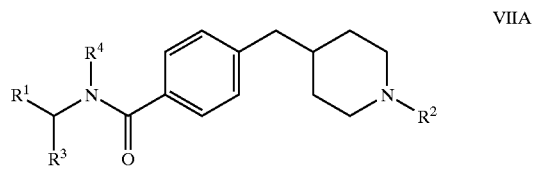

or a pharmaceutically acceptable salt, ester or solvate thereof, wherein $R^1$ is $R^5$—($C_3$–$C_8$)cycloalkyl, $R^5$—($C_3$–$C_8$)cycloalkyl($C_1$–$C_6$)alkyl, $R^5$-aryl, $R^5$-aryl-($C_1$–$C_6$)alkyl or $R^5$-heteroaryl;

$R^2$ is H, ($C_1$–$C_6$)alkyl, $R^6$—($C_3$–$C_8$)cycloalkyl, $R^6$—($C_3$–$C_8$)cycloalkyl-($C_1$–$C_6$)alkyl, $R^6$-heterocycloalkyl, $R^6$—($C_6$–$C_{10}$)bridged cycloalkyl, or $R^6$-bridged heterocycloalkyl;

$R^3$ is $C_1$–$C_6$ alkyl or —$CH_2OH$;

$R^4$ is H or $C_1$–$C_6$ alkyl;

$R^5$ is 1–4 substituents independently selected from the group consisting of H, $C_1$–$C_6$ alkyl, halogen, —OH, $C_1$–$C_6$ alkoxy, $CF_3$, —CN, —$CO_2R^4$, —$CONHR^4$, —$SO_2NHR^4$, —$NHSO_2R^4$ and —$NHC(O)R^4$; and $R^6$ is 1–4 substituents independently selected from the group consisting of H, $C_1$–$C_6$ alkyl, halogen, —OH, $C_1$–$C_6$ alkoxy, $CF_3$, —$NH_2$, ($C_1$–$C_6$)alkylamino, phenyl, $C_1$–$C_2$ alkylenedioxy, and ($C_1$–$C_6$)alkoxycarbonyl.

U.S. Provisional Application No. 60/328,356, filed Oct. 10, 2001 discloses compounds having the following structure:

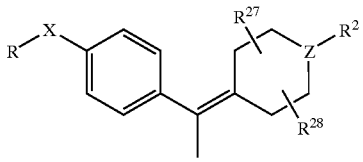

including enantiomers, stereoisomers, rotamers, tautomers and prodrugs of said compound, or pharmaceutically acceptable salts, esters or solvates of said compound or of said prodrugs, wherein:

Z is N, CH, or C-alkyl;

X is —O—, —S—, —SO—, —SO$_2$—, —CO—, —CH$_2$—, or —CS;

R is

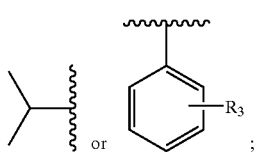

$R^2$ is

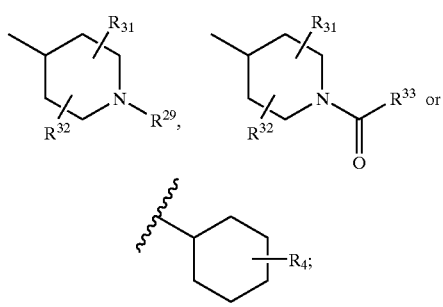

$R^3$ is alkoxy or halo;

$R^4$ is hydrogen, alkyl or alkylhalide;

$R^{27}$ and $R^{28}$ are independently selected from the group consisting of H, alkyl, hydroxyalkyl, arylalkyl, aminoalkyl, haloalkyl, thioalkyl, alkylthioalkyl, carboxyalkyl, imidazolylalkyl, and indolylalkyl; or $R^{27}$ and $R^{28}$ may combine to form an alkylene group;

$R^{29}$ is H, alkyl, —CO-alkyl, —CO-cycloalkyl, alkoxycarbonyl, amino-carbonyl, aryloxycarbonyl, alkylaminocarbonyl, dialkylaminocarbonyl, alkylsulfonyl, arysulfonyl or —SO$_2$—NH—R$^{35}$;

$R^{31}$ and $R^{32}$ are each independently H, alkyl, aryl, cycloalkyl, hydroxyalkyl, or aminoalkyl, and in addition, $R^{31}$ and $R^{32}$ can form the group —(CH$_2$)$_r$—(wherein r is 1 to 6), in further addition, $R^{31}$ and $R^{32}$ can also be hydroxy, —N(R $^{35}$)$_2$, —O-acyl, —N(R$^{35}$)acyl, —OCOOR$^{35}$, or —OCON(R$^{35}$)$_2$;

$R^{33}$ is aryl or heteroaryl, with the proviso that when $R^{33}$ is heteroaryl, the CO—R$^{33}$ bond is to a carbon atom in the R$^{33}$ group; and $R^{35}$ is H, aryl or alkyl.

Preferred m$_2$ antagonists are those claimed in U.S. Pat. No. 6,043,255.

An especially preferred m$_2$ antagonist has the structure

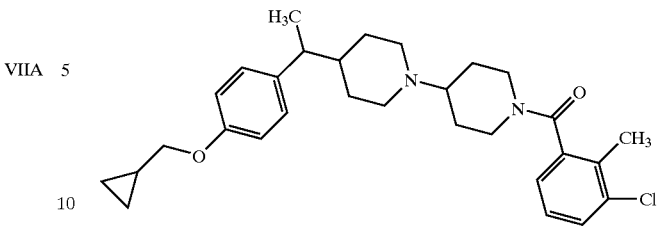

The U.S. patents and applications cited herein are incorporated herein by reference.

Other m$_2$ antagonists can be identified by the test methods described below.

The H$_3$ antagonist and m$_2$ antagonist compounds are prepared by known methods. The dual H$_3$/m$_2$ antagonists listed above are prepared by methods described in the m$_2$ antagonist patents listed above.

The combination of H$_3$ and m$_2$ antagonists can also comprise more than one H$_3$ antagonist (e.g., 2–3) and/or more than one m$_2$ antagonist (e.g., 2–3).

In the aspect of the invention relating to a combination of a dual H$_3$/m$_2$ antagonist in combination with an acetylcholinesterase inhibitor, or a combination of an H$_3$ antagonist and a m$_2$ antagonist with an acetylcholinesterase inhibitor, examples of acetylcholinesterase inhibitors are donepezil, heptylphysostigmine, tacrine, rivastigmine and galantamine.

Test Methods:

Compounds can readily be evaluated to determine activity at H$_3$ receptors by known methods, including the guinea pig brain membrane assay and the guinea pig neurogenic ileum contraction assay, both of which are described in U.S. Pat. No. 5,352,707. Another useful assay utilizes rat brain membranes and is described by West et al., "Identification of Two H$_3$-Histamine Receptor Subtypes," *Molecular Pharmacology*, Vol. 38, pages 610–613 (1990).

A particularly useful screening assay measures binding to sites in guinea pig brain membranes. This test is described in detail by Korte et al., "Characterization and Tissue Distribution of H$_3$ Histamine Receptors in Guinea Pigs by N$^\alpha$-Methylhistamine," in *Biochemical and Biophysical Research Communications*, Vol. 168, pages 979–986 (1990), and quantifies the displacement of bound radiolabeled N$^\alpha$-methylhistamine from tissues by candidate compounds. Results are expressed as "K$_i$" values, in nanoMolar (nM) units, which values can be considered as being dissociation constants for the H$_3$ antagonist on the H$_3$ receptor system, or an index of antagonist affinity for the receptor. In general, K$_i$ values less than about 200 nM are considered necessary for an agent to be useful as an H$_3$ antagonist in the invention. More preferably, the agent will exhibit K$_i$ values of 100 nM or less.

The compound of interest also is tested for its ability to inhibit binding to the cloned human m$_1$, m$_2$ and m$_4$ muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homogenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 μg of protein assay for the $m_1$, $m_2$, and $m_4$ containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985).

Affinity values ($K_i$) are determined using the following formula;

$$K_i = \frac{IC_{50}}{1 + \left[\frac{\text{concentration of radioligand}}{\text{affinity } (K_D) \text{ of radioligand}}\right]}$$

Hence, a lower value of $K_i$ indicates greater binding affinity.

To determine the degree of selectivity of a compound for binding the $m_2$ receptor, the $K_i$ value for $m_1$ receptors was divided by the $K_i$ value for $m_2$ (or $m_4$) receptors. A higher ratio indicates a greater selectivity for binding the $m_2$ muscarinic receptor.

The following procedure is used to show that a compound functions as a $m_2$ antagonist.

Surgery: For these studies, male Sprague-Dawley Rats (250–350 g) were anesthetized with sodium pentobarbital (54 mg/kg, ip) and placed on a Kopf sterotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure involved the insertion through the guide cannula of a thin, needle-like perfusable probe (CMA/12,3 mm×0.5 mm) to a depth of 3 mm in striatum beyond the end of the guide. The probe was connected beforehand with tubing to a microinjection pump (CMA/100). Rats were collared, tethered, and, following probe insertion, were placed in a large, clear, plexiglass bowl with litter material and access to food and water. The probe was perfused at 2 μl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 μM neostigmine bromide at pH 7.4). To achieve stable baseline readings, microdialysis was allowed to proceed for 90 minutes prior to the collection of fractions. Fractions (20 μl) were obtained at 10 minute intervals over a 3 hour period using a refrigerated collector (CMA/170 or 200). Four to five baseline fractions were collected, following which the drug or combination of drugs to be tested was administered to the animal. Upon completion of the collection, each rat was autopsied to determine accuracy of probe placement.

Acetylcholine (ACh) Analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluent from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation). Total run time per sample was 11 minutes at a flow rate of 1 ml/min. Retention times for acetylcholine and choline were 6.5 and 7.8 minutes, respectively. To monitor and correct for possible changes in detector sensitivity during chromatography, ACh standards were included at the beginning, middle and end of each sample queue.

Increases in ACh levels are consistent with presynaptic $m_2$ receptor antagonism.

Affinity values for the $H_3$ and $m_2$ receptors were determined for the dual antagonists identified above. The results of the test procedures are as follows:

| Compound Number | $H_3$ Ki | $m_2$ Ki |
|---|---|---|
| 1 | 18 | 0.17 |
| 2 | 140 | 0.01 |
| 3 | 500 | 0.125 |
| 4 | 620 | 3.4 |
| 5 | 430 | 2.6 |
| 6 | 160 | 1.2 |
| 7 | 22 | 0.07 |
| 8 | 6 | 0.05 |
| 9 | 290 | 0.22 |
| 10 | 15 | 0.019 |
| 11 | 8 | 0.018 |
| 12 | 170 | 4.8 |
| 13 | 12 | 0.8 |
| 14 | 2 | 0.7 |
| 15 | 43 | 0.17 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound or combination is administered orally.

Preferably, the pharmaceutical preparation comprising a dual $H_3/m_2$ antagonist is in unit dosage form. In such form, the preparation is subdivided into unit doses containing appropriate quantities of the active component, e.g., an effective amount to achieve the desired purpose.

The quantity of active dual $H_3/m_2$ antagonist compound in a unit dose of preparation may be varied or adjusted from about 1 mg to 100 mg, preferably from about 1 mg to 50 mg, more preferably about 1 to about 25 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the dual compounds of the invention and the pharmaceutically acceptable salts thereof will be regulated according to the judgment of the attending clinician considering such factors as age, condition and size of the patient as well as severity of the symptoms being treated. A typical recommended dosage regimen for dual $H_3/m_2$ antagonist is oral administration of from 1 mg to 300 mg/day, preferably 1 to 50 mg/day, in two to four divided doses to provide relief from cognition deficit disorders such as Alzheimer's disease.

When the invention comprises a combination of separate $H_3$ antagonist and $m_2$ antagonist compounds, the two active components may be co-administered simultaneously or sequentially, or a single pharmaceutical composition comprising a $H_3$ antagonist and an $m_2$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the $H_3$ antagonist can be determined from published material, and may range from 1 to 1000 mg per dose. The $m_2$ antagonist can be administered in a dosage range of 1 mg to about 100 mg, preferably from about 1 mg. to 50 mg, and more preferably about 1 to about 25 mg. When used in combination, the dosage levels of the individual components are preferably lower than the recommended individual dosages because of the advantageous effect of the combination.

The dosage of the acetylcholinesterase inhibitor used in a combination may range from 0.001 to 100 mg/kg body weight.

When separate $H_3$ and $m_2$ pharmaceutical compositions are to be administered, they can be provided in a kit comprising in a single package, one container comprising an $H_3$ antagonist in a pharmaceutically acceptable carrier, and a separate container comprising a $m_2$ antagonist in a pharmaceutically acceptable carrier, with the $H_3$ and $m_2$ antagonists being present in amounts such that the combination is effective to treat cognition deficit disorders. When an acetylcholinesterase inhibitor is also administered, a separate container comprising an acetylcholinesterase inhibitor in a pharmaceutically acceptable carrier can also be added to the kit. A kit is advantageous for administering a combination when, for example, the components must be administered at different time intervals or when they are in different dosage forms.

The compounds are non-toxic when administered within this dosage range.

The following are examples of pharmaceutical dosage forms which contain a dual compound of the invention, although those skilled in the art will recognize that similar dosage forms will be suitable for separate $H_3$ and $m_2$ antagonists, or for combinations of the separate actives. The scope of the invention in its pharmaceutical composition aspect is not to be limited by the examples provided.

Pharmaceutical Dosage Form Examples

Example A-Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Example A-Tablets

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method of treating Alzheimer's Disease or attention deficit disorder comprising administering to a mammal in need of such treatment an effective amount of a dual histamine $H_3$ receptor antagonist/$m_2$ muscarinic antagonist selected from the group consisting of

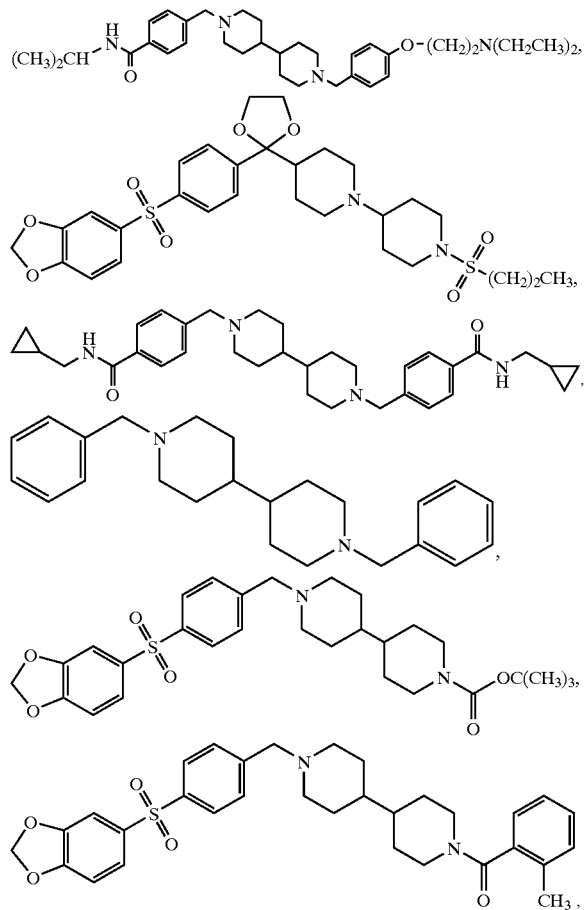

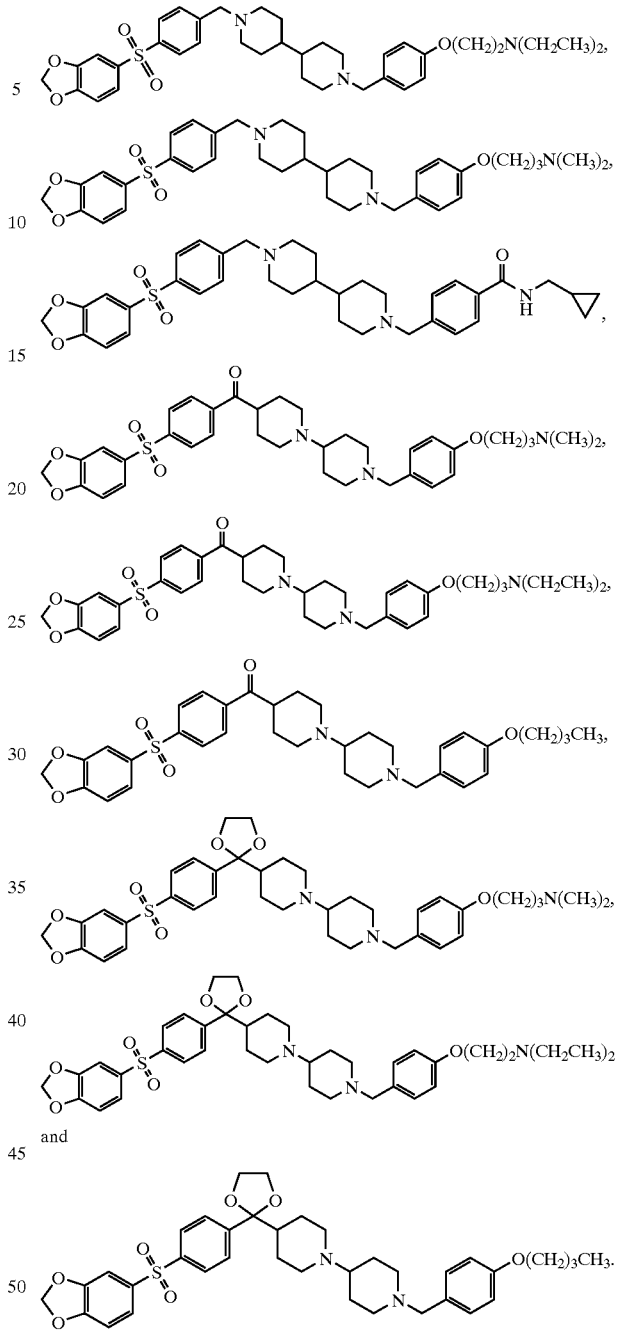

and

2. A method of treating Alzheimer's Disease or attention deficit disorder comprising administering to a mammal in need of such treatment an effective amount of a dual histamine $H_3$ antagonist/$m_2$ muscarinic antagonist of claim 1 in combination with an effective amount of an acetylcholinesterase inhibitor selected from the group consisting of donepezil, heptylphysostigmine, tacrine, rivastigmine and galantamine.

3. A method of treating Alzheimer's Disease or attention deficit disorder comprising administering to a mammal in need of such treatment an effective amount of a dual histamine $H_3$ receptor antagonist/$m_2$ muscarinic a antagonist selected from the group consisting of

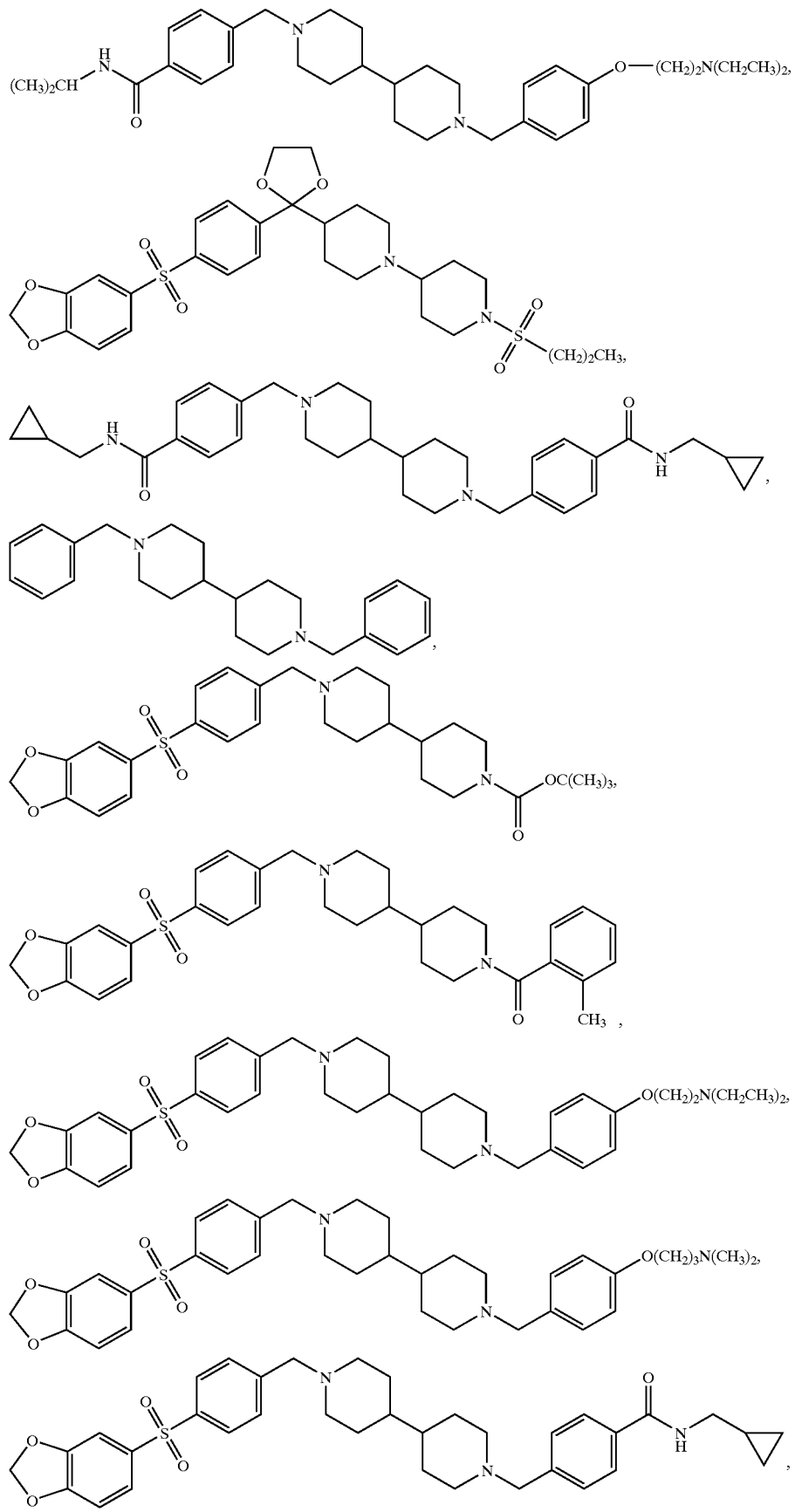

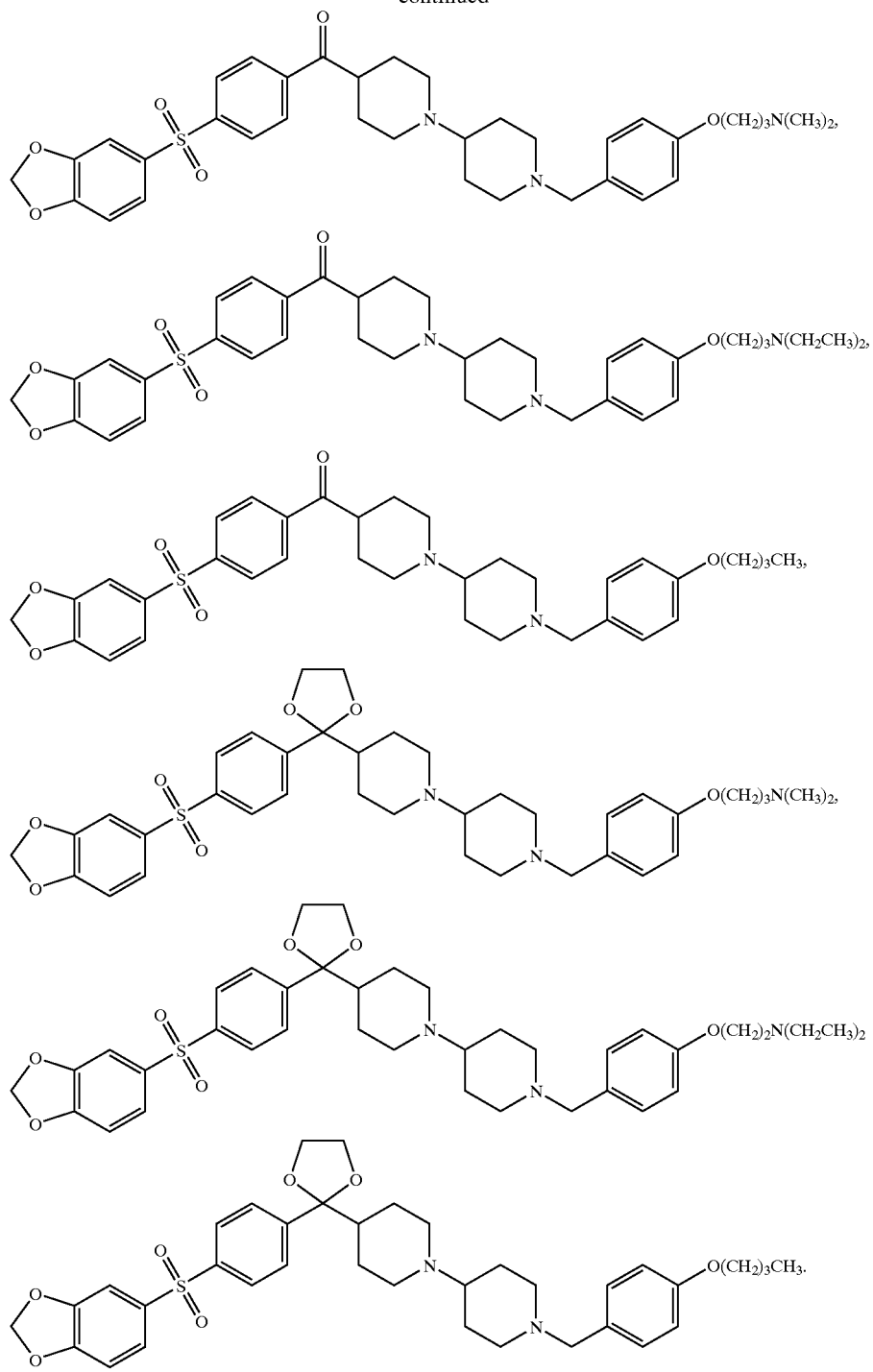

4. A method of treating Alzheimer's Disease or attention deficit disorder comprising administering to a mammal in need of such treatment an effective amount of a dual histamine $H_3$ antagonist/$m_2$ muscarinic antagonist of claim 3 in combination with an effective amount of an acetylcholinesterase inhibitor or selected from the group consisting of donepezil, heptylphysostigmine, tacrine, rivastigmine and galantamine.

* * * * *